(12) United States Patent
Hughett et al.

(10) Patent No.: US 6,863,658 B2
(45) Date of Patent: Mar. 8, 2005

(54) AUTOMATED SYSTEM FOR THE RADIATION TREATMENT OF A DESIRED AREA WITHIN THE BODY OF A PATIENT

(75) Inventors: James David Hughett, Lawrenceville, GA (US); Bradford G. Clay, Suwanee, GA (US); Bryan Dale Knodel, Flagstaff, AZ (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 10/385,107

(22) Filed: Mar. 10, 2003

(65) Prior Publication Data

US 2004/0044305 A1 Mar. 4, 2004

Related U.S. Application Data

(60) Division of application No. 09/522,759, filed on Mar. 10, 2000, now Pat. No. 6,585,684, which is a continuation-in-part of application No. 09/469,510, filed on Dec. 22, 1999, now Pat. No. 6,659,934.

(51) Int. Cl.[7] ............................................. A61M 31/00
(52) U.S. Cl. ................................ 604/65; 600/7; 600/3; 600/4
(58) Field of Search ............................. 604/65, 66, 67, 604/253, 151, 131; 417/478, 217, 238; 600/3–8, 1, 2; 128/DIG. 12, DIG. 13, DIG. 1

(56) References Cited

U.S. PATENT DOCUMENTS

| | | |
|---|---|---|
| 2,750,517 A | 6/1956 | Baum |
| 2,965,761 A | 12/1960 | Horvath |
| 3,088,032 A | 4/1963 | Brunton |
| 3,532,888 A | 10/1970 | Masefield et al. |
| 4,233,517 A | 11/1980 | van't Hooft |
| 4,584,991 A | 4/1986 | Tokita et al. |
| 4,613,325 A | 9/1986 | Abrams |
| 4,673,927 A | 6/1987 | Cianciavicchia et al. |
| 4,710,163 A | 12/1987 | Butterfield |
| 4,733,653 A | 3/1988 | Leung et al. |
| 4,745,907 A | 5/1988 | Russel, Jr. et al. |
| 4,762,518 A | 8/1988 | Kreinick |
| 4,878,896 A | 11/1989 | Garrison et al. |
| 4,898,576 A | 2/1990 | Philip .......................... 604/505 |
| 4,994,035 A | 2/1991 | Mokros ...................... 200/83 J |
| 5,026,348 A | 6/1991 | Venegas ...................... 128/13 |
| 5,030,194 A | 7/1991 | van't Hooft |
| 5,032,113 A | 7/1991 | Burns |

(List continued on next page.)

FOREIGN PATENT DOCUMENTS

| | | |
|---|---|---|
| CA | 1 197 631 | 12/1985 |
| DE | 1 095 963 | 12/1960 |
| GB | 1 219 604 | 1/1971 |
| GB | 1 558 127 | 12/1979 |
| SU | 279 814 | 7/1975 |

OTHER PUBLICATIONS

1) English abstract re German patent application no. DE 1095963, published Dec. 29, 1960.

2) International Search Report re PCT application no. PCT/US99/30000, dated May 31, 2000.

*Primary Examiner*—Manuel Mendez
(74) *Attorney, Agent, or Firm*—Cook, Alex, McFarron, Manzo, Cummings & Mehler, Ltd.

(57) ABSTRACT

A system comprising a microprocessor-controlled transfer device and a separate catheter for intraluminal treatment of a selected site in a body of a patient by at least one treating element advanced from a removable treating element cartridge received in the transfer device into a lumen of the separate catheter by means of pressurized fluid controlled by a fluid control switch moveable between send and return positions, and a safety interlock for use with the system.

6 Claims, 34 Drawing Sheets

U.S. PATENT DOCUMENTS

| | | |
|---|---|---|
| 5,103,395 A | 4/1992 | Spako et al. |
| 5,147,282 A | 9/1992 | Kan |
| 5,342,298 A | 8/1994 | Michaels et al. ............... 128/1 |
| 5,356,378 A | 10/1994 | Doan .......................... 128/13 |
| 5,360,320 A * | 11/1994 | Jameson et al. ................ 417/4 |
| 5,372,709 A | 12/1994 | Hood |
| 5,423,746 A | 6/1995 | Burkett et al. |
| 5,437,634 A | 8/1995 | Amano |
| 5,474,683 A | 12/1995 | Bryant et al. |
| 5,501,665 A | 3/1996 | Jhuboo et al. |
| 5,533,969 A | 7/1996 | Mulder |
| 5,573,502 A | 11/1996 | LeCocq et al. |
| 5,662,611 A | 9/1997 | Beiser et al. |
| 5,683,345 A | 11/1997 | Waksman et al. |
| 5,800,383 A | 9/1998 | Chandler et al. |
| 5,810,770 A | 9/1998 | Chin et al. |
| 5,851,172 A | 12/1998 | Bueche |
| 5,894,273 A | 4/1999 | Meador et al. |
| 5,899,882 A | 5/1999 | Waksman et al. |
| 5,992,686 A * | 11/1999 | Cline et al. ..................... 222/1 |
| 6,013,020 A | 1/2000 | Meloul et al. |
| 6,030,359 A | 2/2000 | Nowosielski ............... 604/131 |
| 6,048,300 A | 4/2000 | Thornton et al. |
| 6,302,864 B1 | 10/2001 | Nowosielski ................ 604/13 |
| 6,585,684 B1 * | 7/2003 | Hughett et al. ............... 604/65 |
| 6,659,934 B1 * | 12/2003 | Hughett et al. ................. 600/7 |

* cited by examiner

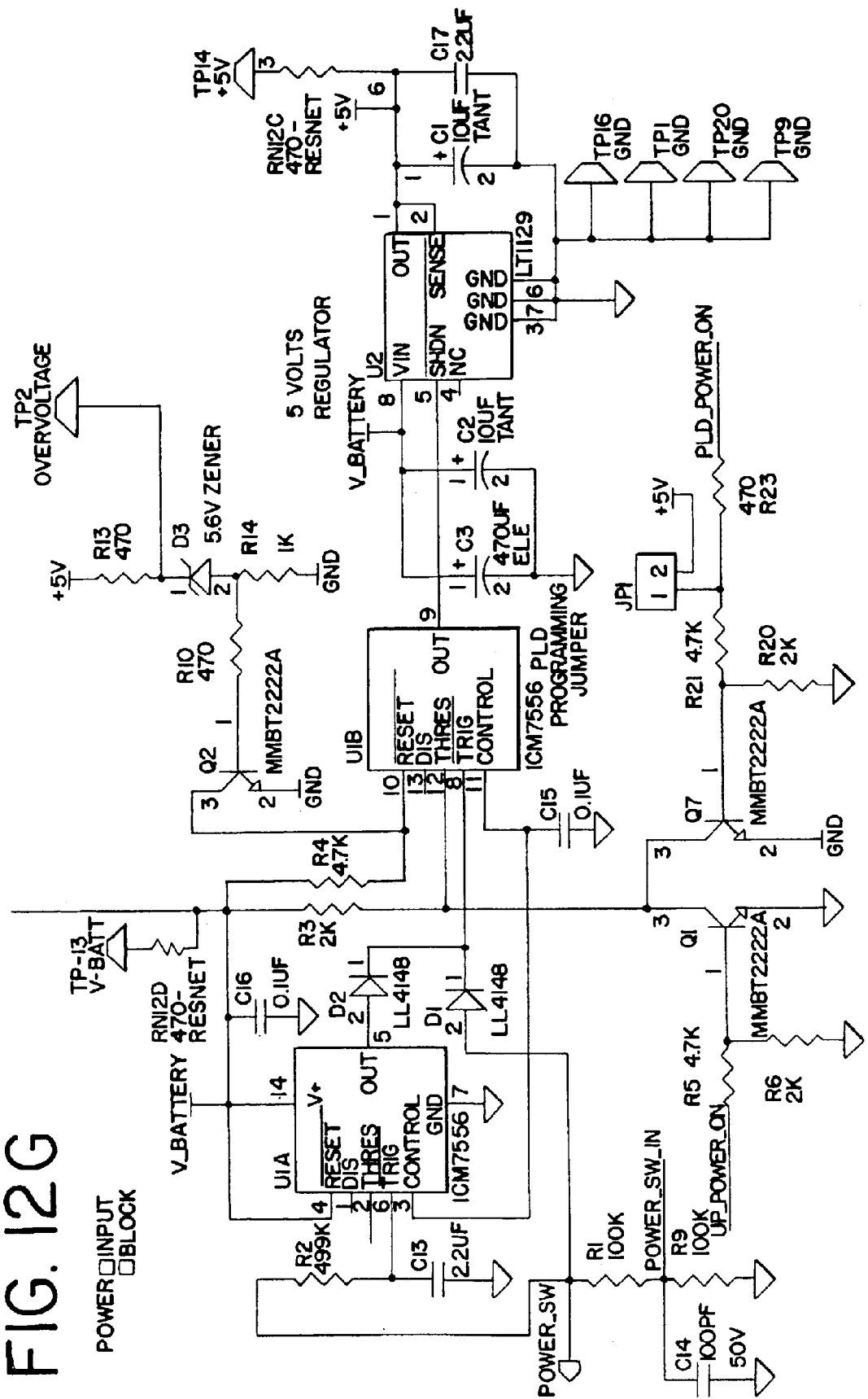

AUTOMATED SYSTEM FOR THE RADIATION TREATMENT OF A DESIRED AREA WITHIN THE BODY OF A PATIENT

CROSS-REFERENCE TO RELATED PATENTS AND APPLICATIONS

This application is a divisional of U.S. application Ser. No. 09/522,759, filed on Mar. 10, 2000 now U.S. Pat. No. 6,585,684.

Application Ser. No. 09/522,759 is a continuation-in-part of U.S. application Ser. No. 09/469,510 filed on Dec. 22, 1999 now U.S. Pat. No. 6,659,934.

The disclosures of U.S. Pat. Nos. 5,683,345, issued Nov. 4, 1997; 5,899,882 issued May 4, 1999; 6,013,020 issued Jan. 11, 2000; U.S. patent applications Ser. Nos. 09/304,752, filed May 4, 1999; 09/469,510 filed Dec. 22, 1999; and U.S. provisional applications Ser. Nos. 60/143,730, filed Jul. 14, 1999; 60/157,496, filed Oct. 4, 1999; and 60/178,962, filed Feb. 1, 2000 are incorporated herein by reference.

BACKGROUND OF THE INVENTION

The present invention relates generally to an intraluminal radiation system for the delivery of treatment elements by way of a catheter to a selected location within the intraluminal passageways of a patient. More particularly, the present invention relates primarily to an improved transfer device for handling the treatment elements and delivering them to the catheter.

Since the late 1970's balloon angioplasty techniques have become widely used for opening blockages in coronary arteries. Briefly, the enlargement of the artery is achieved by advancing a balloon catheter into a narrowed portion of the artery and inflating the balloon to expand the diameter of the artery, thus opening the artery for greater blood flow. Atherectomy techniques, in which blockages are removed or reduced in size, have also been used to the same end.

While balloon angioplasty has proved an effective way of opening the coronary arteries, in a significant number of cases the arteries narrow again at the location where the balloon was expanded, such narrowing being termed restenosis. Restenosis is believed to be caused by formation of scar tissue at the site of the angioplasty that results from the injury to the artery caused by the inflation of the balloon. More recently, intraluminal radiation has been used after angioplasty or atherectomy to treat the affected area of the artery to inhibit cell proliferation and wound healing response and, consequently, help to prevent restenosis. Methods and apparatus for such intraluminal radiation treatment are disclosed in U.S. Pat. Nos. 5,899,882 and 6,013,020, and co-pending applications Ser. No. 09/304,752, filed May 4, 1999, and Ser. No. 09/469,510, filed Dec. 22, 1999, all of which are incorporated herein by reference. These applications generally disclose an apparatus comprising a catheter, which is inserted intraluminally into the patient and advanced to the site of the area to be treated, and a transfer device for facilitating either the hydraulic or pneumatic advancement and retrieval of individual radioactive treating elements or "seeds" along the catheter to and from the treatment site. A plurality of treatment elements comprises a "source train."

As with any device inserted into the vascular system, it must have sufficient integrity to insure that no pieces or elements are separated from or exit the device into the vascular system. This is particularly true for the treating elements which are moved to and from the distal end of the catheter. Additionally, because the device is intended to use radioactive treating elements, there is a heightened need for safety to prevent any unintended exposure of either the patient or the user to radioactivity.

Actual use of the apparatus described in the above-identified patents and co-pending applications has suggested several areas where the device could be improved to reduce the possibility of having treatment elements escape from the system, thus enhancing patient and user safety.

Consequently, it is the principal object of the present invention to provide a transfer device and catheter assembly that has additional safeguards to protect the patient and user for unintended exposure to radiation.

More particularly, it is an object of the present invention to provide a transfer device/catheter assembly in which the treatment elements cannot be inadvertently released from the transfer device.

Additionally, it is an object of the present invention to provide a transfer device capable of advancing and retrieving source trains of varying lengths for treatment of different sized lesions. More particularly, the transfer device is adapted to receive interchangeable cartridges which house source trains of varying lengths.

Another object of the present invention is to provide a delivery system that requires both automation and manual manipulation to successfully and safely advance the user through the treatment procedure. More particularly, the transfer device automatically creates the pressurized fluid flow, senses the presence or absence of the treating elements within the transfer device, and permits or prevents movement of the gate mechanism to the open or closed position through the use of electromechanical means and prompts the user to sequentially follow the appropriate manual steps for safely providing treatment to the patient.

SUMMARY OF THE INVENTION

These objects, as well as others which will become apparent upon reference to the following drawings and detailed description, are provided by a system comprising a microprocessor-controlled transfer device and a separate catheter for intraluminal treatment of a selected site in a body of a patient by at least one treating element advanced from a removable treating element cartridge received in the transfer device into a lumen of the separate catheter by means of pressurized fluid controlled by a fluid control switch moveable between send and return positions. A safety interlock is provided for preventing both (1) the disassembly of the system unless the treating element resides in the treating element cartridge and (2) the actuation of the fluid control switch unless the system is assembled. The safety interlock comprises a first lock moveable from a first position to a second position only if both the catheter and the treating element cartridge are secured to the transfer device. The first lock blocks the movement of the fluid control switch to the send position when in its first position and prevents disassembly of either the catheter or the treating element cartridge from the transfer device when in its second position. The fluid control switch further locks the first lock into its second position when the fluid control switch is in the send position.

In a preferred embodiment, the safety interlock comprises a spring having two arms, each arm being engaged by one of the catheter or the treating element cartridge when attached to the transfer device. A slidable switch is provided including a yoke that is moveable from a first position to a second position to capture the arms of the spring and to lock both the catheter and the treating element cartridge to the transfer device only if each arm of the spring is engaged by one of the catheter and treating element cartridge. Each arm of the spring is independently capable of blocking movement of the yoke from its first position to its second position if the spring arm is not engaged by one of the catheter or treating element cartridge.

The fluid control switch actuates a gate mechanism moveable between open and closed positions to respectively permit or prevent the treating element from moving out of the treating element cartridge when subjected to pressurized fluid. A solenoid is provided to lock the gate mechanism in the open position and disengages the gate mechanism to permit it to close only when the treating element resides in the treating element cartridge.

Photo interrupters or other sensors may be associated with the first lock or the fluid control switch to detect their position and generate a signal sent to the microprocessor to permit the treatment to continue in accordance with the position of the first lock and the fluid control switch.

In a further aspect of the invention, a system is provided for detecting whether the treating element resides at a targeted location along the lumen of the transfer device. The detection system comprises a pressure transducer that is in fluid communication with the lumen of the transfer device so as to be capable of measuring the fluid pressure difference across the targeted location of the lumen circuitry is provided for comparing the measured pressure difference to a reference pressure difference corresponding to the pressure difference at the targeted location when the treating elements are stored at the targeted location under fluid pressure. A signal generator provides a signal when the measured pressure difference differs from the reference pressure difference by more than a predetermined amount. The signal may activate an optical signal and/or a mechanical interlock, the latter preventing separation of the catheter from the transfer device and preventing closure of the gate when activated by a signal from the signal generator corresponding to the pressure difference encountered when the treating element does not reside at the targeted location.

In an alternate embodiment of this aspect of the present invention, the pressure transducer is in fluid communication with the lumen of the transfer device so as to be capable of gauging the fluid pressure at a single point along the lumen of the transfer device and distal to where the treatment elements reside at a targeted location along the lumen of the transfer device. The measured pressure at this single point is compared to either a predefined pressure or a reference pressure corresponding to the pressure at the same point when the treating elements are stored at the targeted location under fluid pressure. A signal generator provides a signal when the measured pressure differs from the predefined or reference pressure by more than a predetermined amount.

BRIEF DESCRIPTION OF THE DRAWINGS

FIGS. 12A–12L are circuit diagrams for the system electronics of the transfer device of FIG. 1.

DETAILED DESCRIPTION OF THE INVENTION

The present invention comprises an automated catheter based radiation delivery system, generally designated 10, and its method of use for treatment of a desired area within the body of a patient. The system includes a delivery catheter 12, a plurality of treatment elements/marker seeds 14 (best seen in FIG. 6) comprising a "source train," and a transfer device 16 that electromechanically delivers the treatment element source train through the catheter 12 to the selected location within a patient's body. The transfer device 16 is controlled by a microprocessor that prompts the user to proceed appropriately through the procedure with a series of individual display prompts, which combine with operative input controls to allow for an intuitive user interface.

Figure 1:
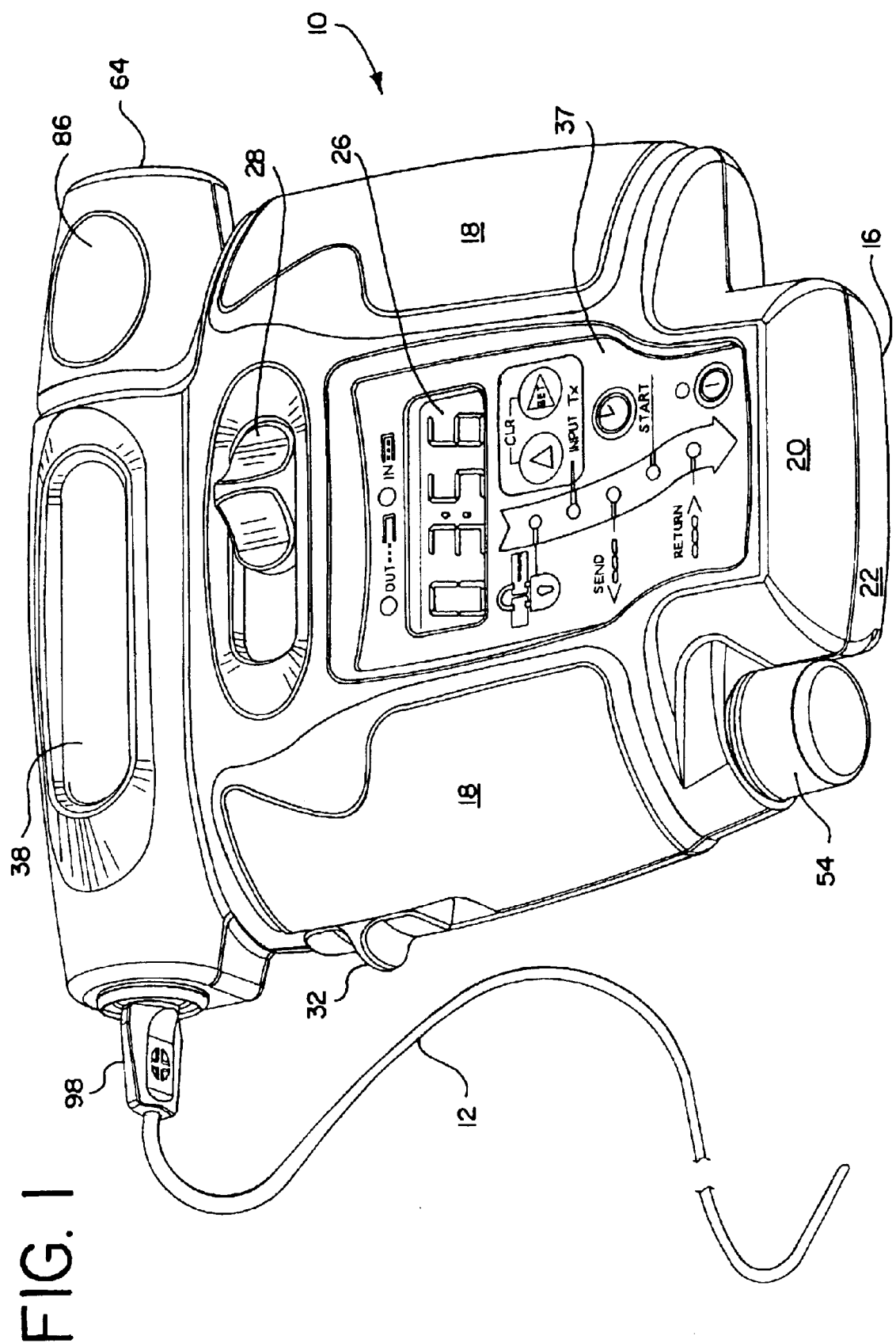
FIG. 1 is a perspective view of a treatment system according to the present invention including a transfer device and a catheter.
Figure 2:
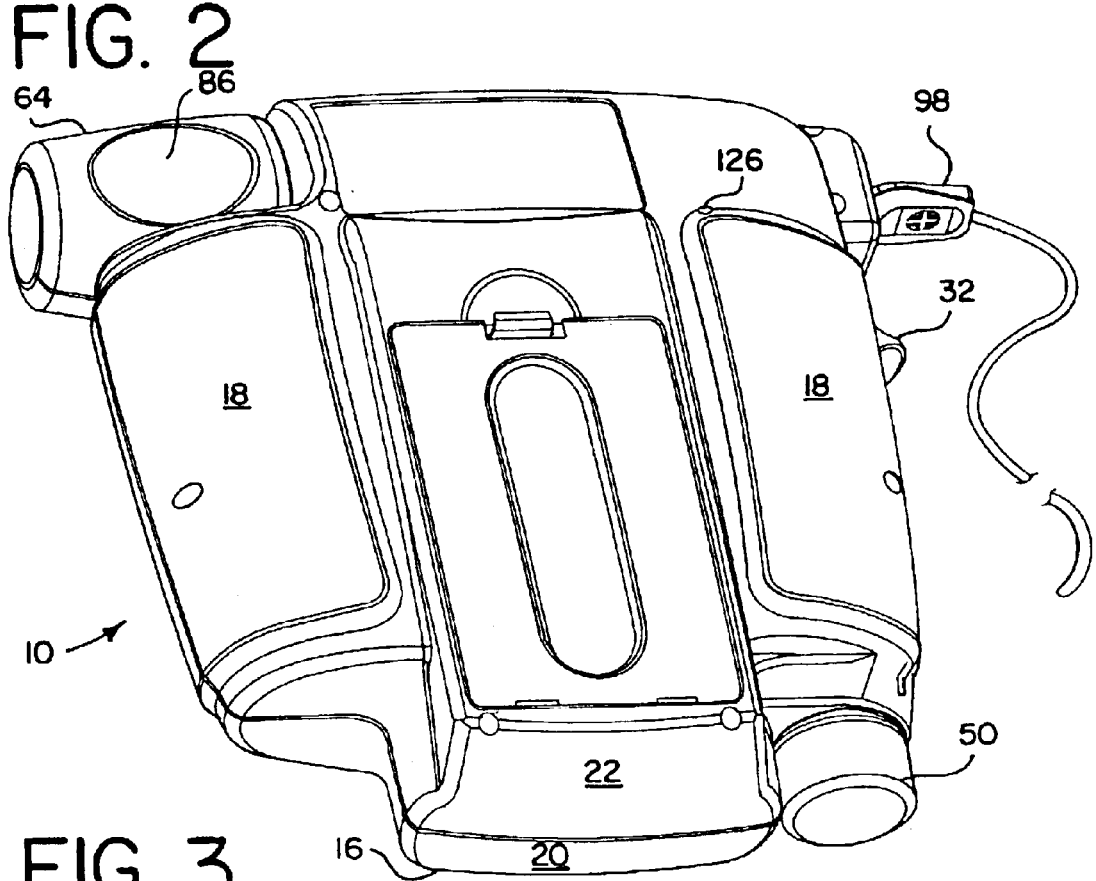
FIG. 2 is a bottom perspective view of the system of FIG. 1.

The assembled transfer device can be seen in FIGS. 1 and 2. The exterior of the transfer device 16 is ergonomically designed to be easily held with either or both hands, making it equally adaptable for right and left-handed clinicians. As can be seen in FIGS. 1 and 2, curved handgrips 18 are located on both the left and right sides of the transfer device 16. Alternatively, the device 10 can rest in the palm of the user's hand or on a flat surface. The controls are easily reachable with the thumbs when both hands are supporting the device.

An upper housing portion 20 and a lower housing portion 22 fit together to create the shell that holds the internal components. An opening 24 (FIG. 4) in the upper housing portion 20 allows a user to view an LED display 26. A fluid control switch 28 extends through a second opening 30 in the upper housing 20, while a safety lock switch 32 extends through complementary openings 34, 36 in the left-hand grip of the upper and lower housing portions 20, 22. Electronic controls are accessed through a membrane keypad 37, which effectively seals the controls from sources of moisture. Alternate keys, buttons, or components may be used to access the electronic controls of the transfer device 16.

Figure 8:
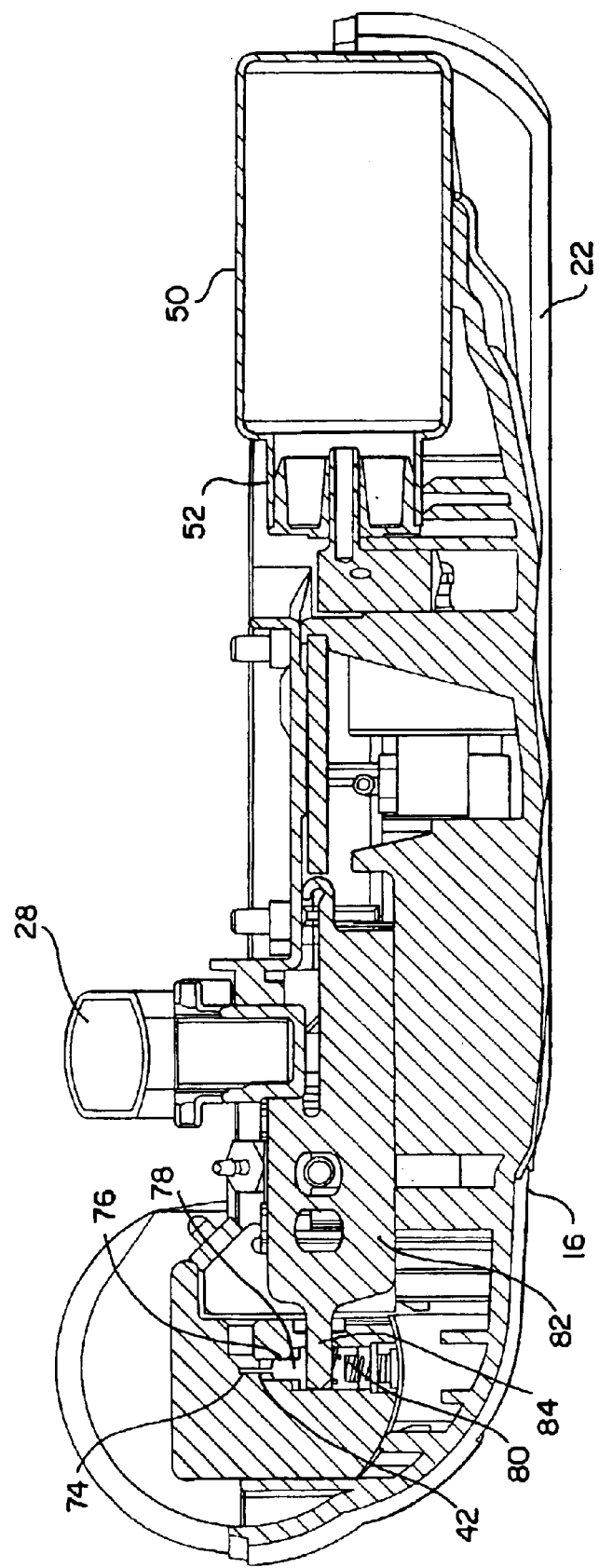
FIG. 8 is a cross-sectional view taken substantially along line 8—8 of FIG. 7.

The upper portion 20 also includes a window 38 for viewing a sleeve 40, which houses the treating element source train (comprising a plurality treatment elements and marker seeds), and a pin gate 42 (FIG. 8). The sleeve 40 is preferably made of a radiation-blocking material, such as quartz, synthetic fused silica, polycarbonate plastic, etc.

Figure 4:
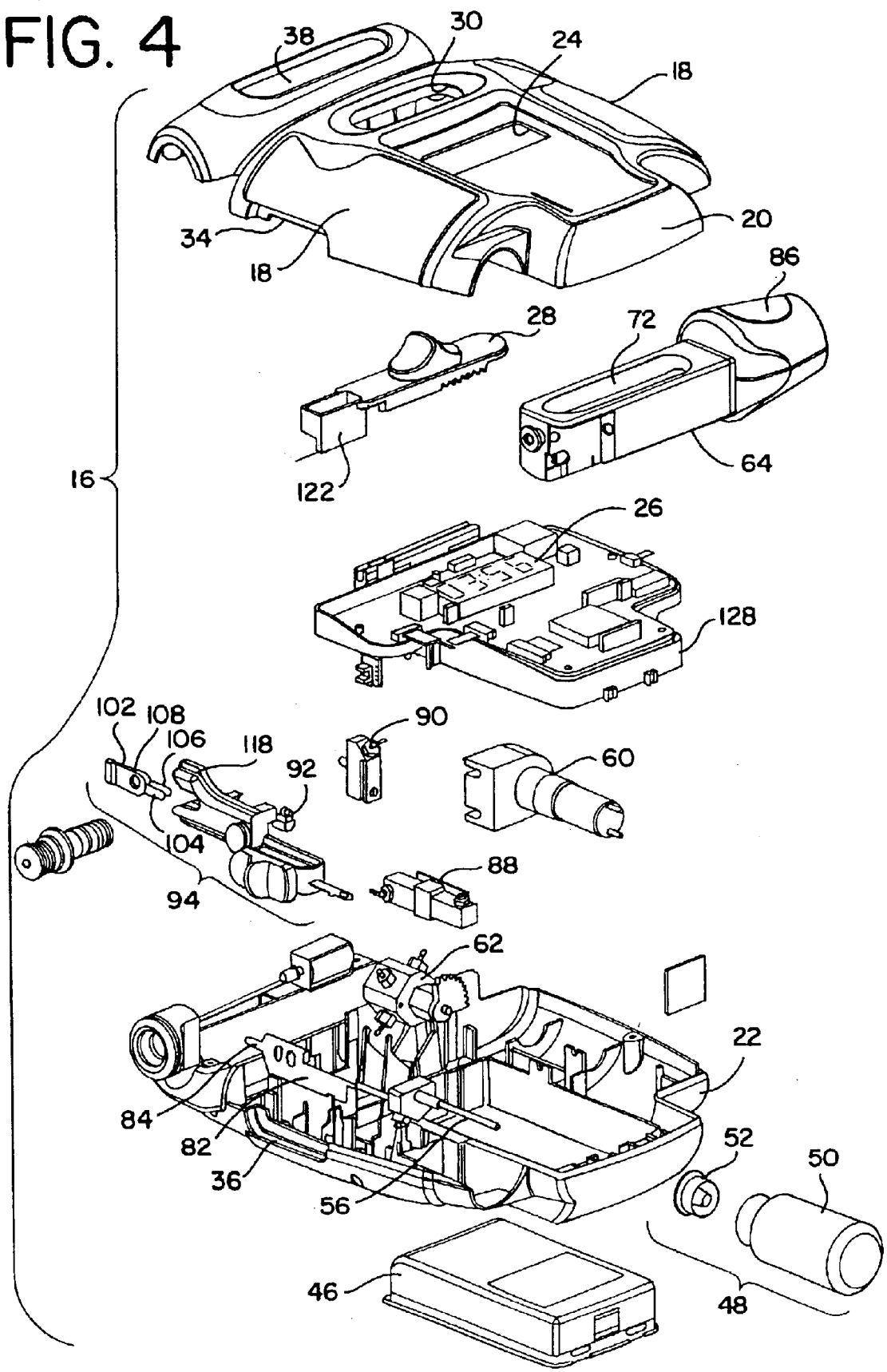
FIG. 4 is an exploded perspective view of the transfer device shown in FIG. 1.

The lower housing portion 22 has a central opening 44 for receiving the power supply for the device, most likely a replaceable or rechargeable battery pack 46 (FIG. 4). The battery pack 46 may have an integrated plastic housing with external contacts (not shown) that connect electrically with similar contacts in the central opening 44. Thus, enclosing the battery pack 46 and making it instantly accessible by the user from the exterior of the transfer device 10, ensures its ease of replacement or recharging. Alternatively, a hard cover (not shown) may be securely positioned over the battery pack 46, completely closing the battery compartment 44.

The upper and lower housing portions 20, 22 together also create an opening for the insertion of a fluid cartridge assembly 48. The fluid cartridge 48 contains saline, sterile, purified, or distilled water, or some other fluid source for the hydraulic or pneumatic delivery of the source train. The fluid cartridge assembly 48 includes a cylindrical fluid reservoir 50, an end cap 52 that channels the fluid in and out of the fluid reservoir 50, and possibly a handle 54 for easier insertion and removal of the fluid reservoir 50 with respect to the transfer device 16. The transfer device 16 has a fluid manifold 58 comprising a fluid pick-up in the form of an elongated appendage 56 (shown schematically in FIG. 9) and having two fluid ports, an inlet 55 and an outlet 57, through which fluid is introduced into and exited from the fluid channels of the transfer device 16, respectively. The end cap 52 has a small opening for receiving the elongated appendage 56 upon the insertion of the fluid cartridge 48 into the transfer device 16 and provides a fluid tight seal around the elongated appendage 56. For a more secure connection, mating threads may be added to the transfer device 16 and the fluid cartridge 48 for screwing the fluid cartridge 48 into the transfer device 16.

The fluid cartridge assembly 48 may be either disposable or removable for cleaning and for replacing the used fluid with fresh fluid. At the end of each treatment, the used, disposable fluid cartridge 48 can be discarded and replaced with a new pre-filled cartridge.

As shown in the fluid flow diagram of FIG. 9, the fluid flow path begins within the fluid reservoir 50 and continues throughout the delivery system. Through the outlet port 57 of the manifold 58, the fluid cartridge 48 is in fluid communication with a peristaltic pump 60, which draws the fluid in and forces it through fluid channels to effectively deliver, maintain, and retrieve the treatment elements. The peristaltic pump 60 can be programmed to operate in a single direction for both sending and retrieving the treatment elements, or can be programmed to alternate directions between the sending and retrieving modes.

When pumping fluid in a single direction, the system relies on a fluid control valve 62, preferably a manual valve operable by the user of the transfer device 16, to properly direct the fluid flow. Alternatively, a solenoid valve could be used to automatically control the direction of the fluid flow. The fluid control valve 62 is in fluid communication with all fluid channels in the transfer device 16, the source cartridge 64 (described in detail below) and the attached delivery catheter 12. In the send mode, the fluid control valve 62 directs the fluid flow through the source cartridge 64, into the catheter through the source delivery lumen, and out of the catheter through the fluid return channel. In the return mode, the fluid control valve 62 reverses the direction of flow.

In use, greater force is required to send and retrieve the treatment elements to and from the catheter than to maintain them at a desired location in the catheter for treatment. Therefore, to conserve energy, the pump 60 operates at a decreased speed when maintaining the position of the treatment elements. When the treatment is complete, the pump 60 resumes full speed to force the treatment elements back into the source cartridge 64 within the transfer device 16. The pump 60 is idle when no treatment elements are being sent, maintained, or retrieved.

Figure 3:
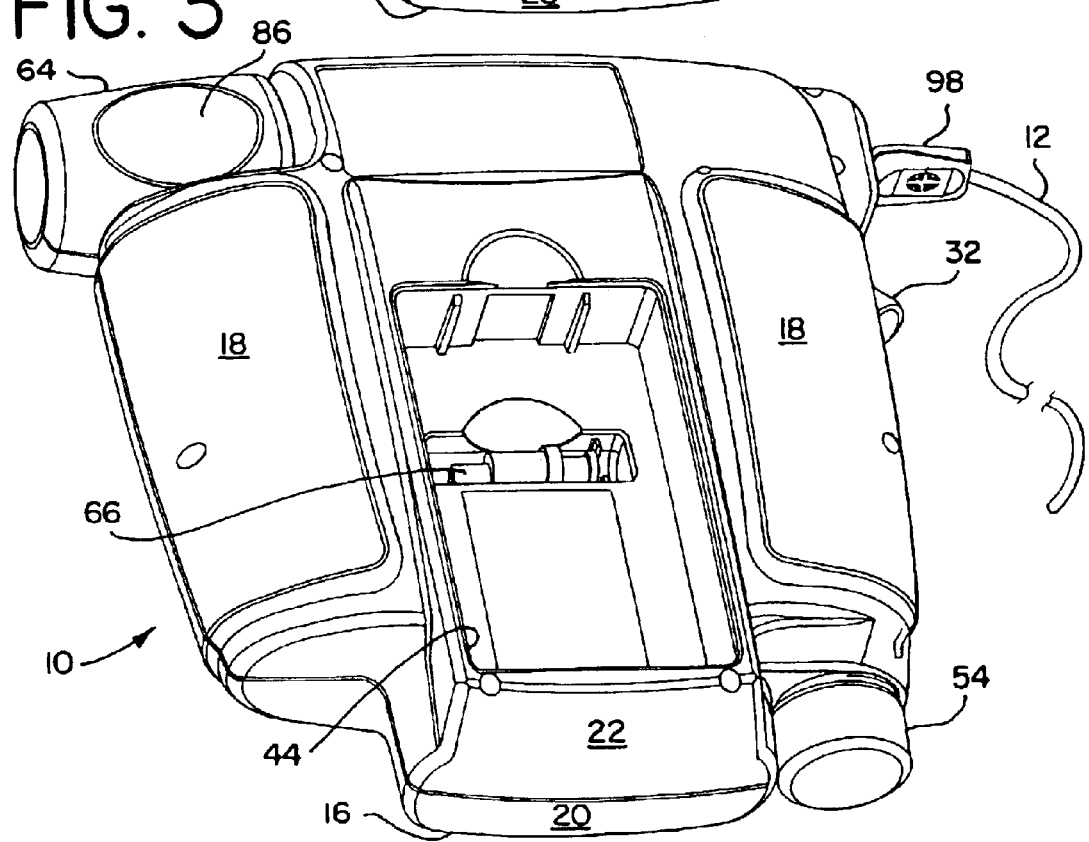
FIG. 3 is a perspective view similar to that of FIG. 2 except that the hatch is removed to show the storage compartment for the battery pack.

In the event the pump 60 becomes inoperable at a time when the treatment elements are not housed within the source cartridge 64, the user may manually override the automatic fluid management system to retrieve the elements. For example, a luer connector 66 (seen in FIG. 3) accessible to the user through the battery compartment 44 may be in fluid communication with the fluid flow path, and a fluid filled syringe (not shown) may be attached to the connector and used as a source of pressurized fluid to force the return of all treatment elements to the source cartridge 64.

Figure 5:
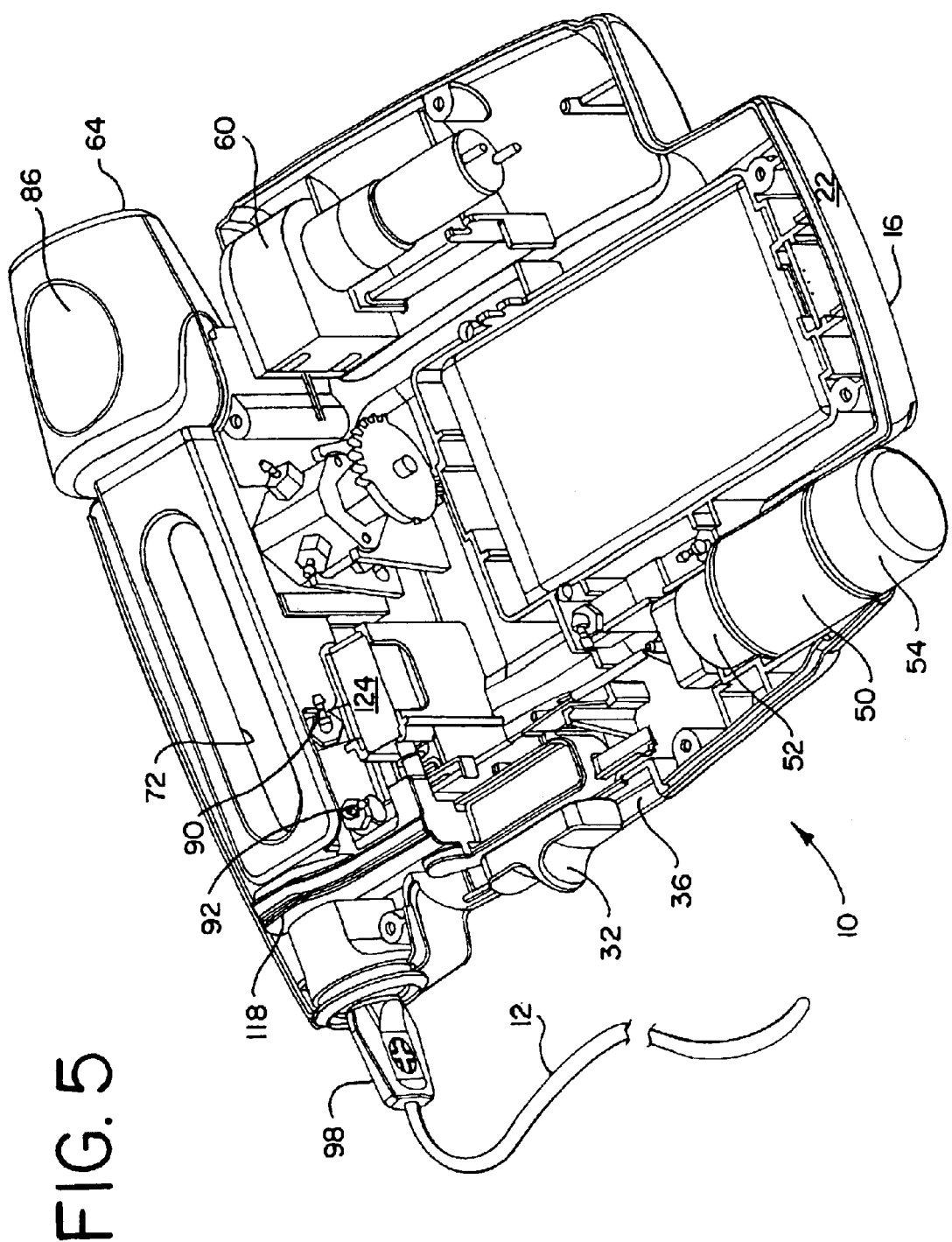
FIG. 5 is perspective view of the transfer device shown in FIG. 1 with the top half removed to show detail.

The source cartridge 64 comprises an interchangeable assembly (best seen in FIGS. 4 and 5). In order to be capable of delivering variable source train lengths, the source cartridge assembly 64 houses the quartz sleeve 40 which has a lumen 70 in which the treating elements/member seeds 14 comprising the source train resides. The pin gate 42 is also integral with the quartz sleeve 40. Interchangeable cartridges 64 housing source trains of different lengths allow the user to select a cartridge having a source train of the appropriate length to treat the patient. Each cartridge 64 has the capability to store a source train of the maximum length contemplated for treatment of either coronary vessels or peripheral vessels. A source train that is shorter than the maximum length is accompanied by a retainer (not shown) that maintains the source train 43 immediately adjacent to the pin gate 42 in the distal end of the lumen 70 in the quartz sleeve. When inserted into the transfer device 16, the source cartridge 64 completes the fluid path by fluidly connecting the fluid control valve 62 to channels within the transfer device 16 and the delivery catheter 12.

With reference to FIG. 5, the top central portion of the source cartridge has an elongated opening 72 that permits the user to view the transparent quartz sleeve 40. A clear window piece fits within the opening 72 for visual detection of the treatment elements/marker seeds 14 and the pin gate 42, which are housed by the quartz sleeve 40. For magnification of the treatment elements and marker seeds, a magnifying lens could replace the entire window. The distal end of the window 40 or magnifying lens may also be coupled to a circular lens to further magnify at least the pin gate 44 and the distal marker seed area of the source train. Alternatively, a magnifying lens may be added to the window 38 of the transfer device 16.

To further enhance the visual detection of the treatment elements 14, back lighting may be added, for example, by including in the source cartridge 64 a light emitting diode coupled to a fiber optics plate or light panel underlying the quartz sleeve 40.

With reference to FIG. 8, the pin gate 42, which is similar to that disclosed within FIGS. 39A and 39B of U.S. application Ser. No. 08/936,058, incorporated by reference above, lies within a channel that is perpendicular to the central lumen 70 and that connects the central lumen 70 to the exterior of the quartz sleeve 40. The pin gate 42 is maneuvered between a closed position, where it intersects the quartz lumen 70 to prevent the source train from exiting the quartz sleeve 40, and an open position, where it retracts to allow the delivery of the source train into the catheter 12. Within an opening in the source cartridge 64 and external to the quartz sleeve 40 rest the remaining components of the pin gate mechanism 42: a pin 74, a seal 76, a bar 78, and a compression spring 80. The pin gate 42 is controlled by a sliding member 82 that has an elongated camming portion 84 that engages the bar 78 to move and maintain the pin gate 42 in the open position (as shown in FIG. 8). When the sliding member 82 is released, the camming portion 84 no longer engages the bar 78 and the pin gate closes.

The source cartridge assembly 64 also includes a large knob-like handle 86 for facilitating easy insertion into and removal from the transfer device 16. The handle 86 may include an indication of the source train length and/or may be color coded to differentiate it from other cartridges 64 that contain different length source trains.

The source cartridge 64 may also include a non-volatile memory that stores specific information regarding the source train, such as its length, its radiation activity, and the number of times it has been used for radiation treatment. The stored data is a compilation of alpha-numeric characters in hexadecimal format. The transfer device 16 may also perform a check on the data to make sure it falls within the designated limits. If the data falls outside the limits, the transfer device 16 will indicate an error and will not allow treatment to begin.

Prior to disconnecting the catheter 12 or source cartridge 64 from the transfer device 16, the user must be assured that all treating,elements are positioned within the quartz housing 40 and behind the closed pin gate 42. This may be done by the visual detection of the source train through the window in the source cartridge 64 that permits viewing of the quartz sleeve 40. Visual detection may be enhanced with the addition of illumination provided by a light emitting diode coupled to fiber optics.

Figure 6:
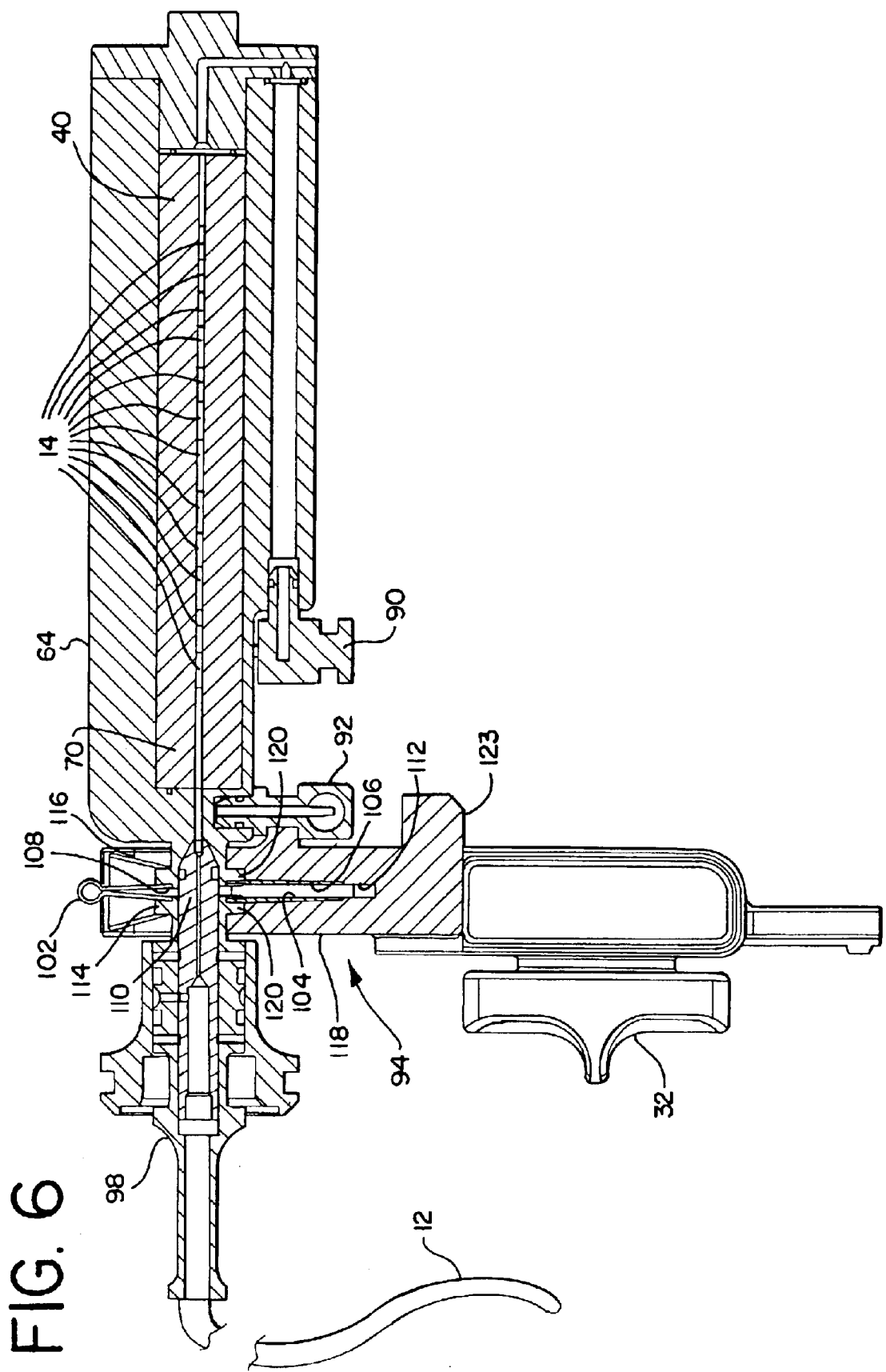
FIG. 6 is an enlarged plan view of the first lock, catheter, and treating element cartridge, in partial cross-section to show detail.
Figure 9A:
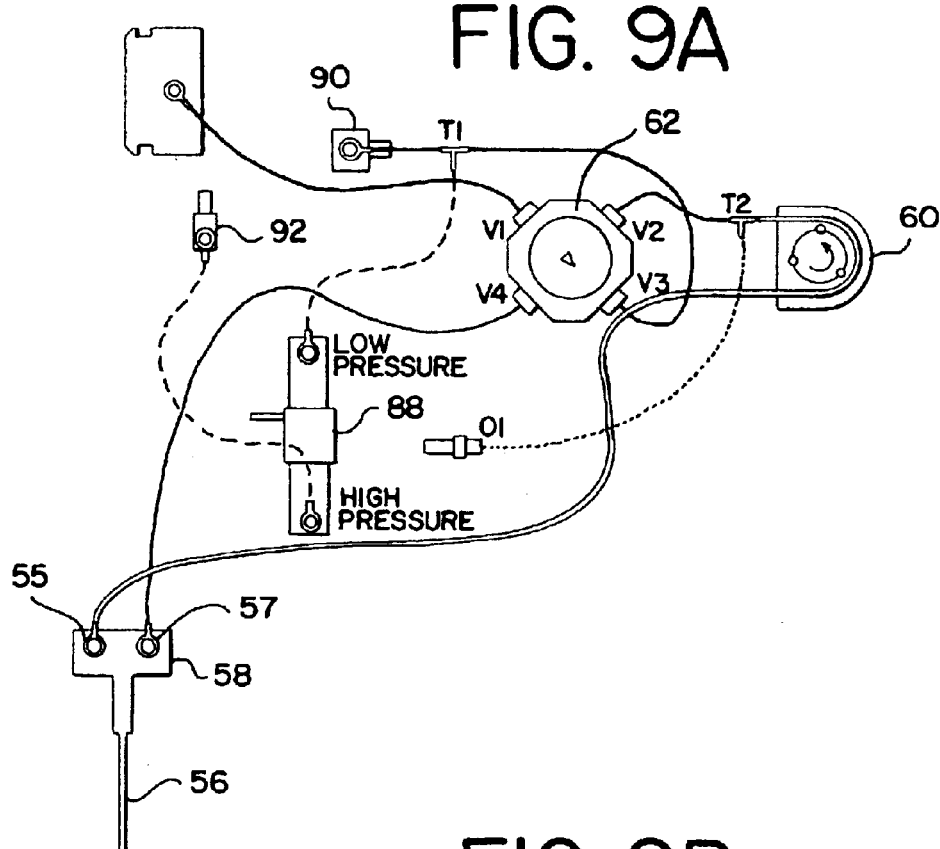
FIGS. 9A and B are schematic views showing the fluid flow path in the transfer device.

However, in accordance with one aspect of the present invention, a seed detection system is provided that determines whether the source train is residing in the lumen of the quartz sleeve between its proximal and distal ends based upon the fluid pressure drop across the lumen 70 in the quartz sleeve 40. With reference to FIGS. 6 and 9A, the seed detection system comprises a pressure transducer 88 in fluid communication with the lumen 70 in the quartz sleeve 40 through access ports 90, 92 at the proximal and distal ends, respectively, of the flow path through the source cartridge 64. Access port 90 connects with the source cartridge 64 upon insertion of source cartridge 64 into transfer device 16. Access port 92 is fixed to the safety interlock 94, described below, and completes the fluid path when the safety interlock 94 is positioned to engage the source cartridge 64 and the catheter 12.

The transducer 88 generates a first or reference signal based upon the pressure drop across the quartz sleeve lumen when all the treating elements/marker seeds of the source train reside in the quartz lumen 70. The pressure transducer 88 continuously measures the pressure drop across the ports 90, 92 and, as can be readily appreciated, if the seeds/markers 14 of the source train reside at a location other than the quartz sleeve 40, e.g., in the catheter 12, the pressure drop across the two ports 90, 92 should be insignificant. The microprocessor which serves to control the transfer device also compares the measured pressure difference to the reference pressure difference and generates a signal when the measured pressure difference differs from the reference pressure difference by more than a predetermined amount, e.g., 10%. This signal may activate an optical signal on the display of the transfer device and/or a mechanical interlock, the latter preventing the separation of the catheter 12 and source cartridge 64 from the transfer device 16 based upon receiving the signal from the signal generator.

In practice, the transducer 88 is self-calibrating so that it is adaptable to measuring the reference pressure drop in the quartz lumen 70 for the source trains of the varying lengths contemplated for use with the transfer device. In practice, a Honeywell "wet-wet" transducer is contemplated for use with respect to differential pressure measuring.

Figure 9B:
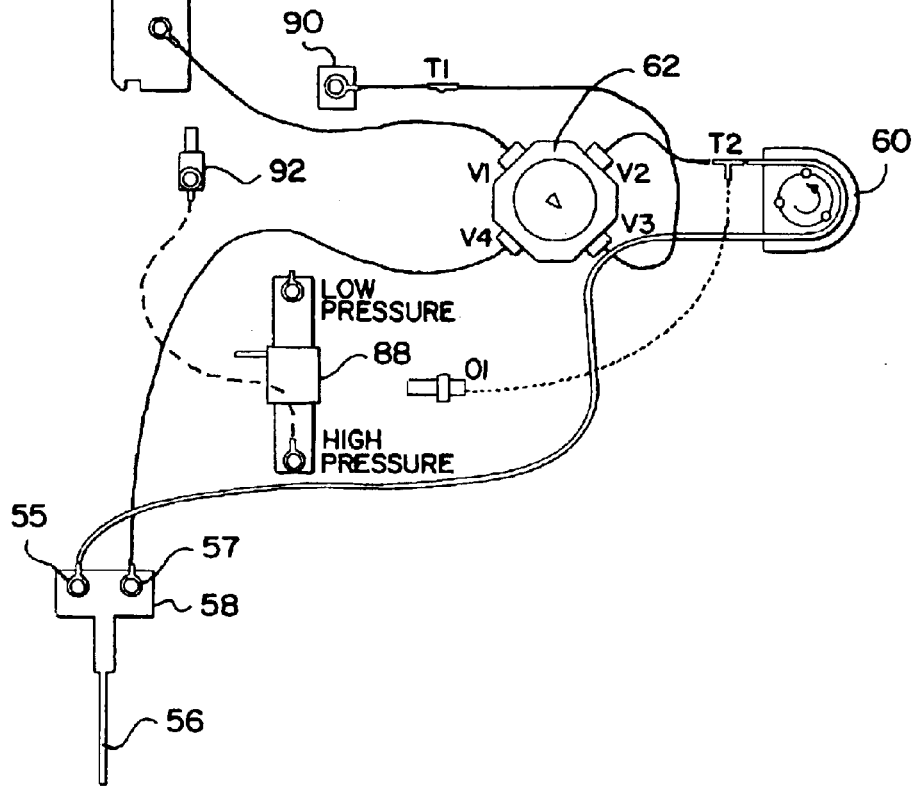

In an alternate embodiment of this aspect of the present invention, as shown in FIG. 9B, the seed detection system comprises a pressure transducer 88 in fluid communication with the lumen 70 in the quartz sleeve 40 through a single access port 92 at the distal end of the flow path through the source cartridge 64. The measured pressure is compared to either a predefined pressure or a reference pressure corresponding to the pressure at the access port 92 when the treating elements 14 are stored at the targeted location under fluid pressure. A signal generator provides a signal when the measured pressure differs from the predefined or reference pressure by more than a predetermined amount. In practice, a Microswitch 27PC Series transducer is contemplated for use with respect to either embodiment of pressure sensing.

In order to ensure that the difference in the pressure drop across the quartz lumen or in the pressure at a single location along the lumen of the transfer device is of a sufficiently different magnitude when the treating elements/marker seeds are not in the quartz lumen, the treating elements/marker seeds 14 may be joined together so that they move as a unit in and out of the quartz sleeve. This helps prevent false readings from occurring if, e.g., most, but not all, of the individual treating elements/marker seeds 14 are returned to the quartz sleeve 40 lumen after concluding a treatment procedure.

In addition to the pressure differential detection system for sensing the presence of the source train, other sensors may be included within the transfer device 16 to detect the presence of the fluid cartridge 48, source cartridge 64, and catheter 12. Such sensors may be any of a number of well-known types, such as mechanical, electromechanical (e.g., a leaf spring with a microprocessor measuring its movement or detecting its position), electrical (e.g., a trip switch or limit switch), magnetic (e.g., a reed switch with a permanent magnet), electromagnetic (e.g., Hall effect sensors), or optical sensors. Other types of sensors include displacement and position sensors, proximity sensors, occupancy motion detectors, pressure sensors, and force or strain sensors.

In the illustrated embodiment, for each of the three connections, an optical sensor can be coupled with an illumination source, such as an infrared LED. The illumination sources would be positioned such that each of the fluid cartridge 48, source cartridge 64, and catheter 12 break the light beam of its illumination source when properly connected to the transfer device 16. The sensor detects the change in the amount of projected light and communicates this with the electronic controls of the system. If one or more of the fluid cartridge 48, source cartridge 64, and delivery catheter 12 are not properly connected to the transfer device 16, a graphic user interface may display the missing connection(s) and will not allow the user to proceed further until corrected.

In accordance with another feature of the present invention, a safety interlock is provided for preventing both (1) the disassembly of the catheter and source cartridge from the transfer device unless all of the treating elements/marker elements 14 reside in the source cartridge 64 and (2) the actuation of the fluid control valve to the "send" position unless the system is assembled.

With reference to FIG. 4, a safety interlock 94 including a slidable switch 32 is provided that mates with both a connector 98 at the proximal end of the delivery catheter 12 and the source cartridge 64 when they are connected to the transfer device 16. If the safety interlock is not mating with both the connector 98 on the delivery catheter 12 and the source cartridge 64, it is positioned to block movement of a fluid control switch 28 that controls the fluid control valve 62 so that the fluid control valve 62 cannot be moved to the "send" position. Conversely, when the safety interlock 94 mechanism is engaging both the connector 98 on the delivery catheter 12 and the source cartridge 64, the fluid control switch 28 blocks movement of the slidable switch 32 to the position in which the catheter connector 98 and the source cartridge 64 are released.

Figure 7:
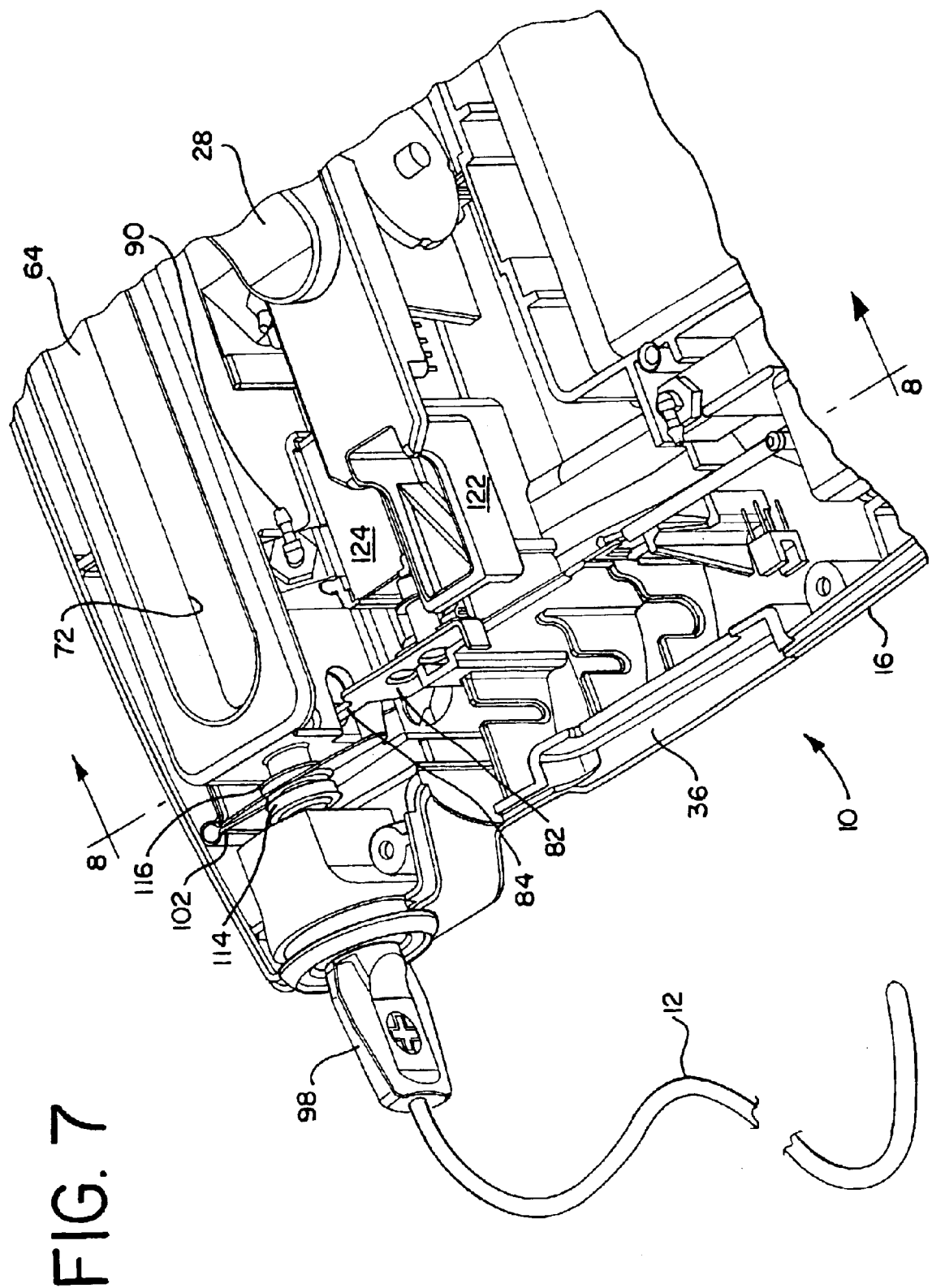
FIG. 7 is a fragmentary perspective view of the transfer device showing the relationship between the gate mechanism and the treating element cartridge.

As best seen with reference to FIG. 6, the safety interlock 94 includes a spring 102 having two arms 104, 106 and a central aperture 108 that receives a protruding part 110 of the catheter connector 98. When the catheter connector 98 and the source cartridge 64 are properly seated in the transfer device 16, each engages and compresses an arm 104, 106 of the spring 102 and moves the two arms 104, 106 towards each other against the spring pressure. This permits the arms of the spring to be received in an internal slot 112 on the switch 32 so that the switch 32 can be slid into locking engagement with a hub portion 114, 116 on each of the catheter connector 98 and source cartridge 64, respectively. Specifically, the switch includes a yoke member 118 that captures the hubs of the connector and the source cartridge when the spring is depressed by the proper seating of the catheter and the source cartridge. The hubs 114, 116 are received in a shoulder 120 on the mouth of the slot 112. If either of the catheter connector 98 or the source cartridge 64 is not properly seated and its spring arm 104 or 106 not depressed, the spring arm 104 or 106 will engage the shoulder 118 at the mouth of the slot 112, preventing the switch 32 from sliding into the locking position and, consequently blocking movement of the fluid control switch 28 to the "send" position. With reference to FIG. 7, the fluid control switch 28 also includes an arm 122 that engages a shoulder 123 (FIG. 6) on the switch 32 when the switch 32 is in its locking position and the fluid control switch 28 is in the "send" position, thus preventing release of the catheter 12 and source cartridge 64 from the transfer device 16 when in this mode.

To provide further insurance against the unintended or improper operation of the treatment system, the fluid control switch 28 may be associated with a solenoid 124 that locks the pin gate mechanism 74–82 in the open position and permits it to close only when the treating elements/marker seeds reside in the treating element cartridge. The solenoid 124 may be operated by, e.g., the treating element detection system described above.

In the event the pump 60 becomes inoperable or there is an electronics failure at a time when the treatment elements 14 are not housed within the source cartridge 64, the user may manually override the automatic fluid management system to retrieve the elements 14 as described above. To secure the manually retrieved treatment elements 14 within the source cartridge 64 by closing the pin gate 42 will also require a feature for overriding the solenoid 124. An opening 126 (FIG. 2) in the transfer device 16 is the gateway to manually manipulating the solenoid 124. When a pin is inserted into opening 126, it displaces a component having a ramped edge (not shown) in such a manner as to retract the solenoid plunger from the sliding member 82 and permit the pin gate to close.

Additionally, a sensor, preferably a photo interrupter, can be associated with the switch 32, the photo interrupter being triggered when the switch 32 is moved to the locking position. The triggered photo interrupter generates a signal which is transmitted to the microprocessor that permits the treatment to continue. Similar photo interrupters may be associated with the fluid control switch to detect its position and generate a signal sent to the microprocessor that permits the treatment to continue in accordance with the position of the fluid control switch. While photo interrupters are the preferred sensors, numerous other types of sensors, such as those described above, may be used in place of the photo interrupters.

The transfer device 16 can be connected to any of the catheters that are disclosed in the patents and applications previously incorporated herein by reference. Catheters may be constructed of any material, or a combination of materials, such as nylon, PEBAX, polyimide, polyethylene, and polyurethane.

The treatment elements/marker seeds 14 of source train may also be any of those described in the patents and applications previously incorporated herein by reference. A source train consists of a series of treatment elements and two marker seeds, one at each end of the source train. Preferably, the treatment elements are radioactive cylinders. The marker seeds are used to properly position the treatment elements at the treatment site and are preferably platinum, platinum-iridium, gold or gold plated, since each of these is highly visible under fluoroscopy, which is used to monitor the radiation therapy.

Figure 10A:
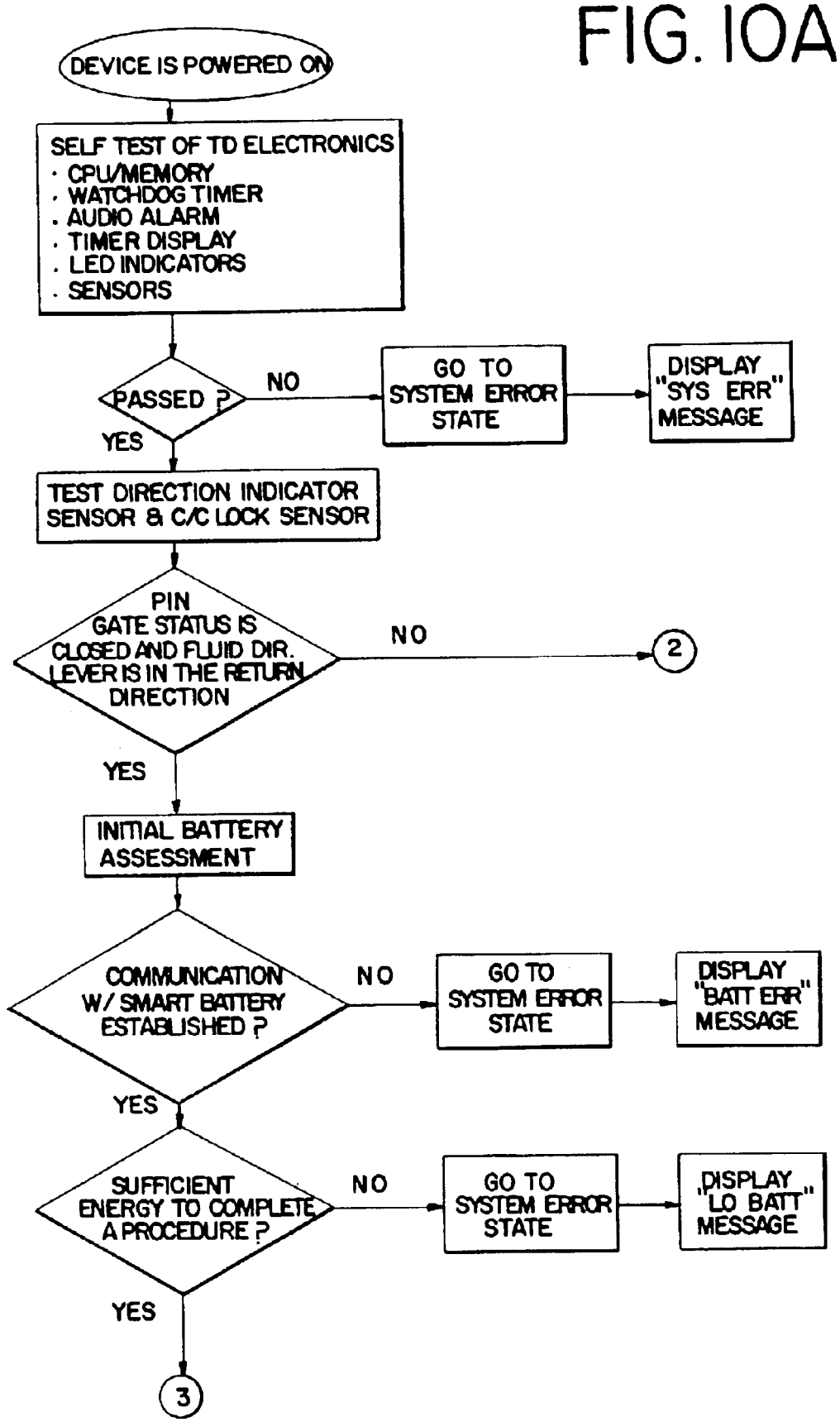
FIGS. 10A–M comprise a flow chart illustrating the logic utilized by the microprocessor to conduct an interactive treatment with the intraluminal treatment system described herein based upon commands input by the user.
Figure 10B:
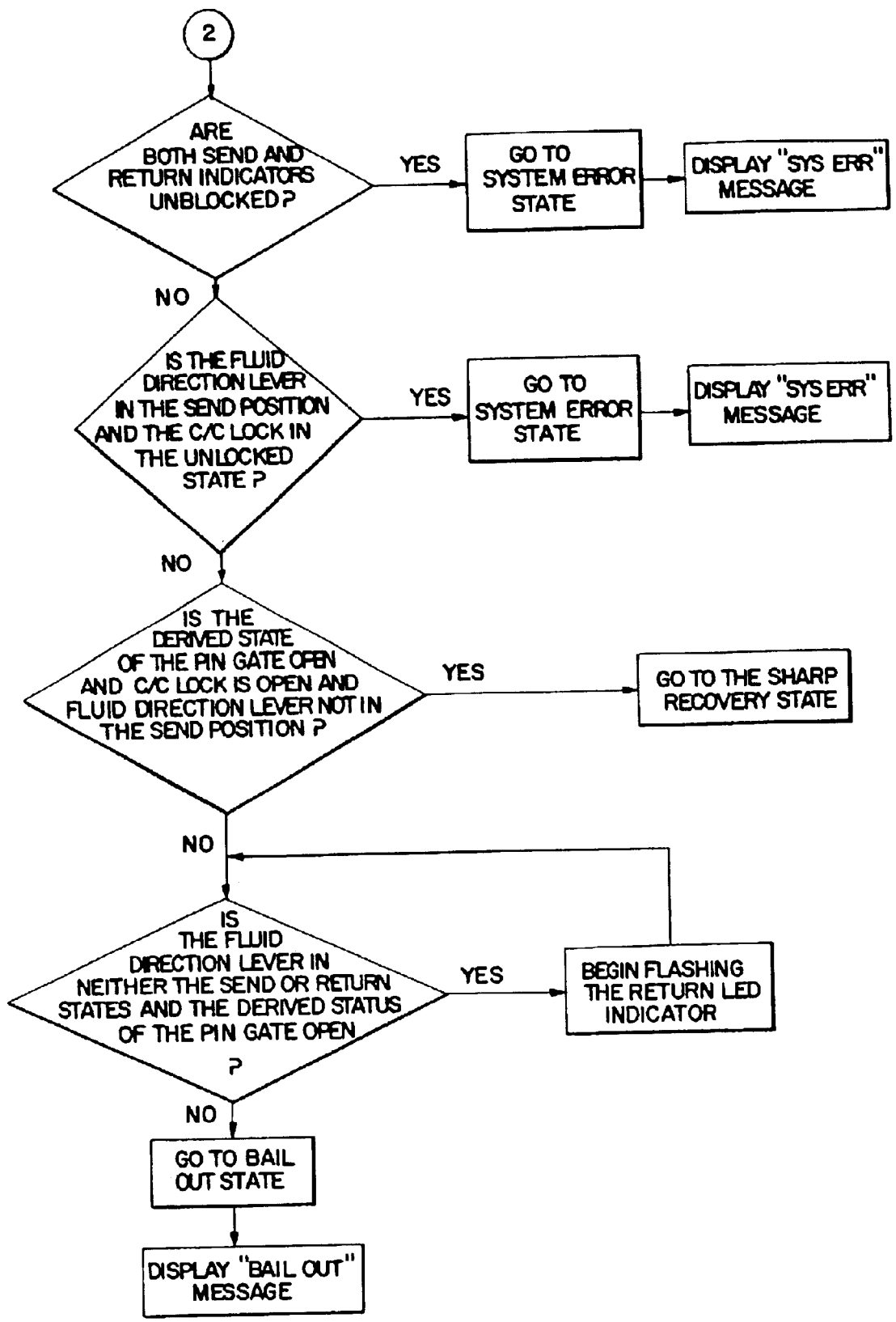
Figure 10C:
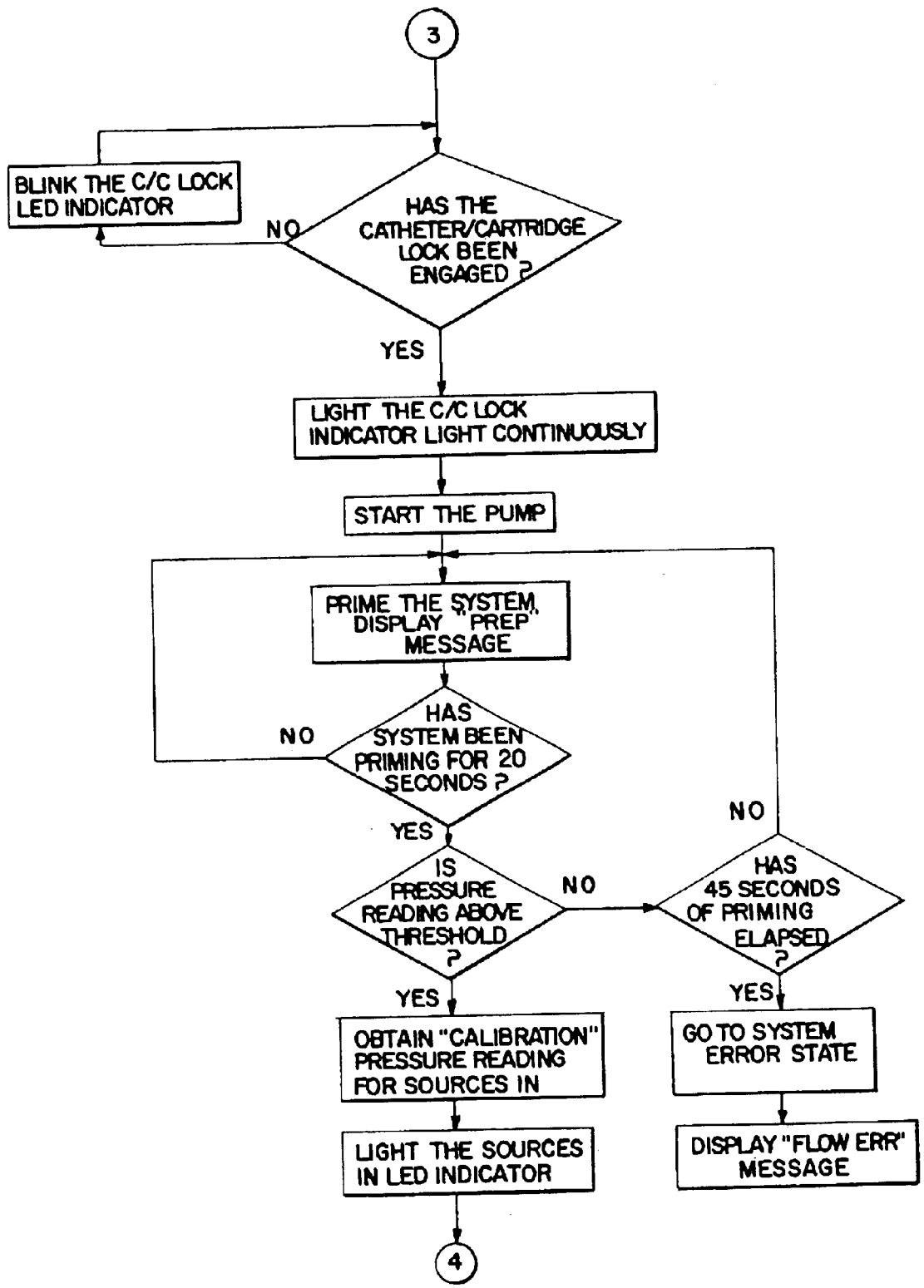
Figure 10D:
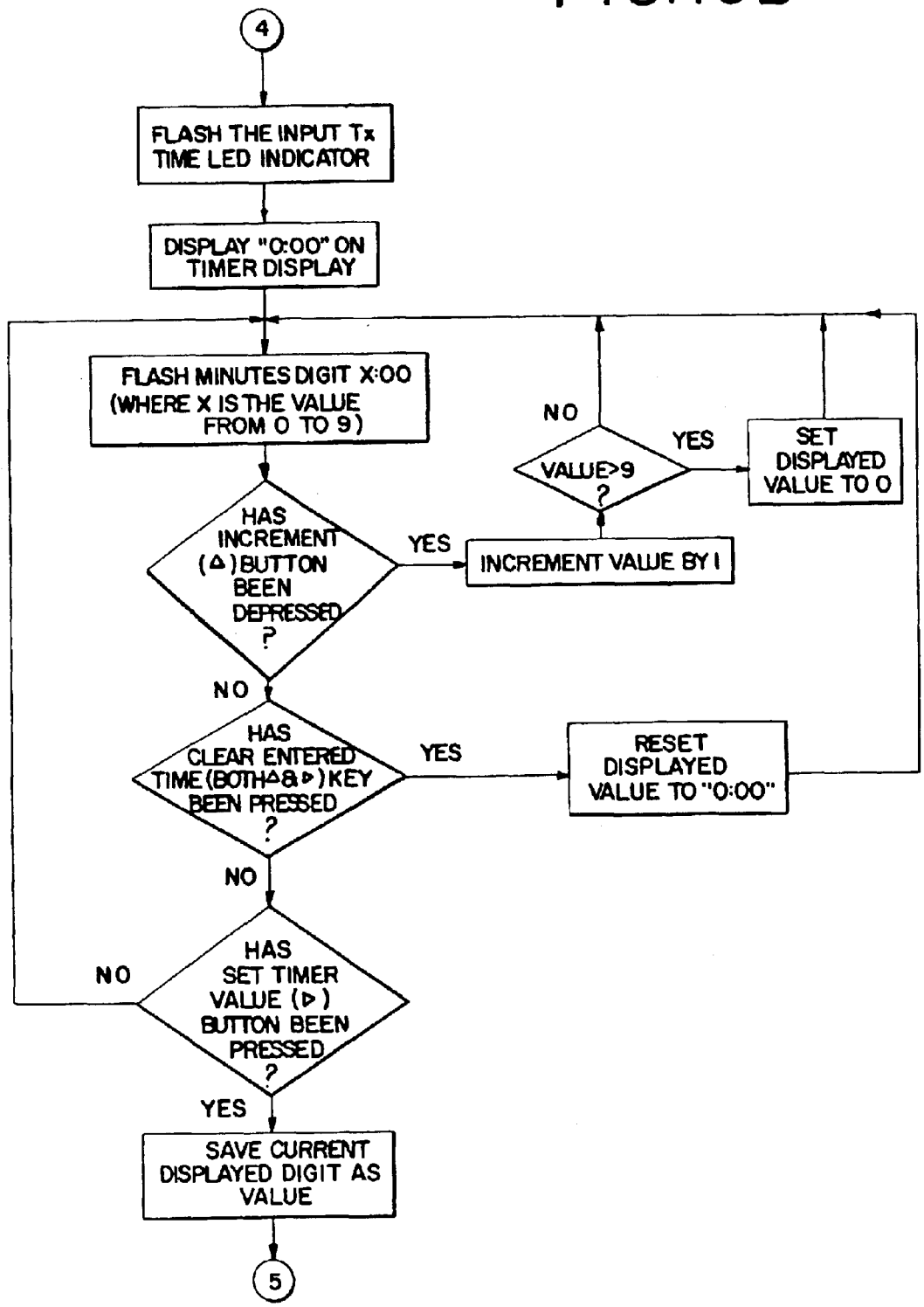
Figure 10E:
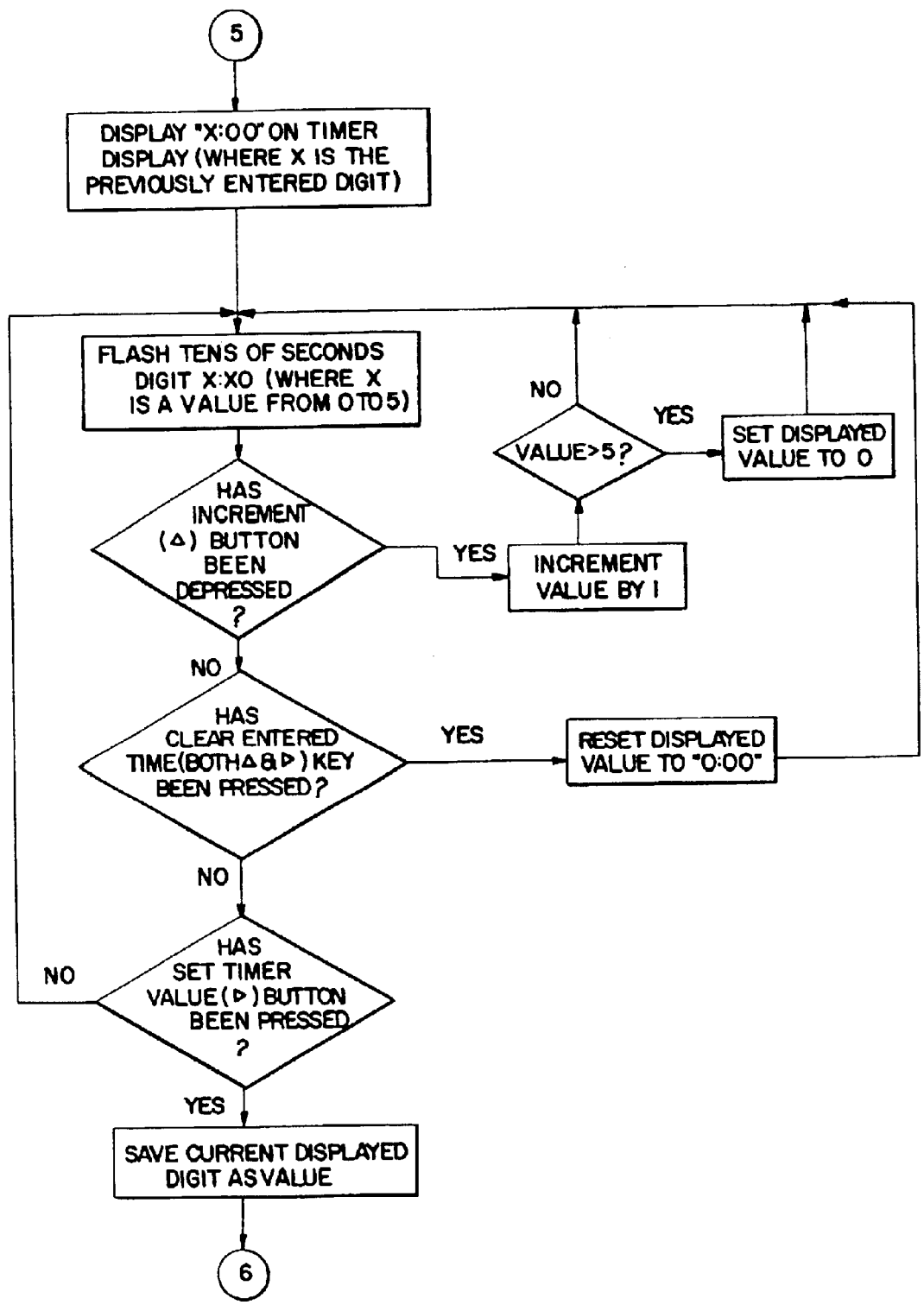
Figure 10F:
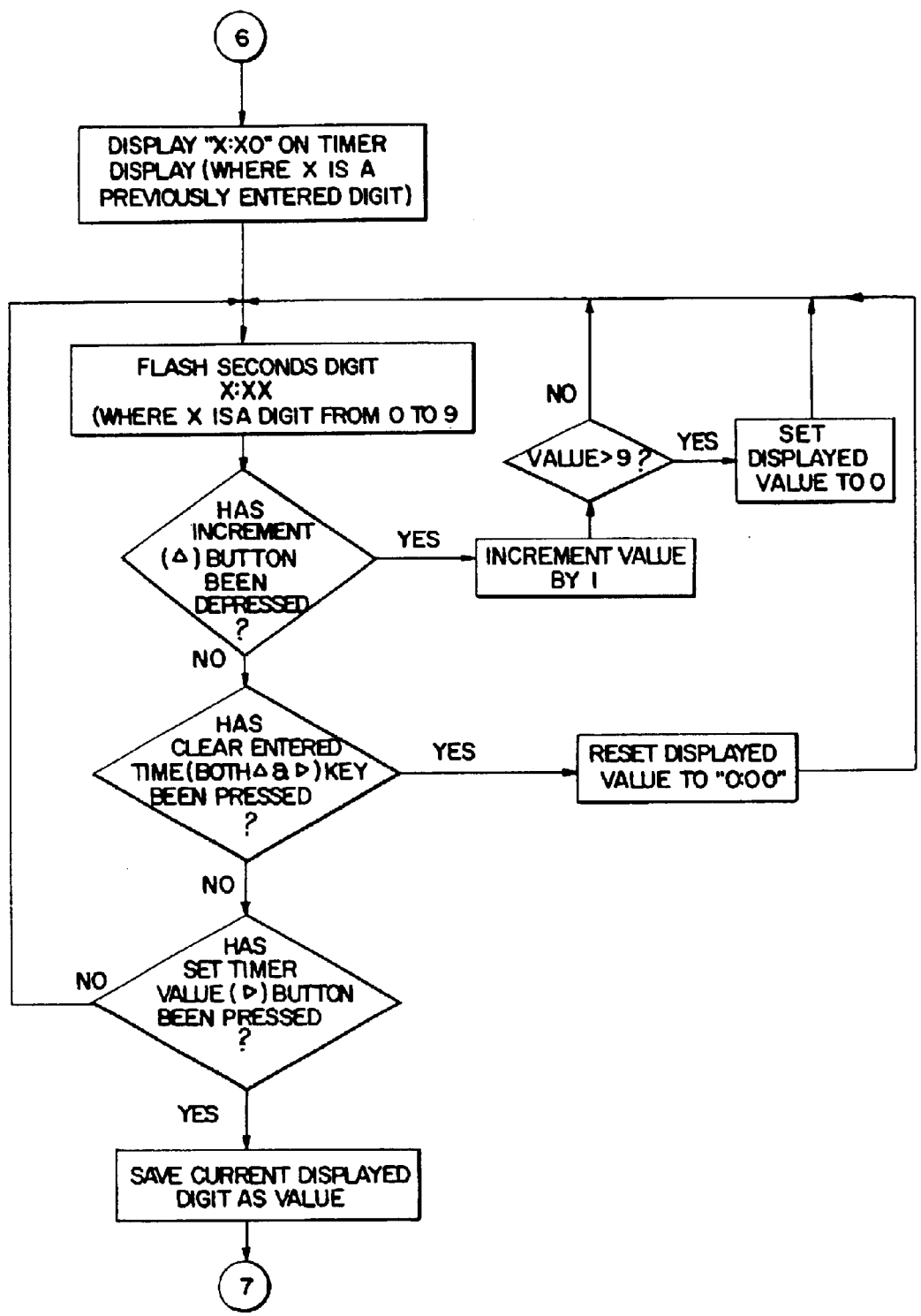
Figure 10G:
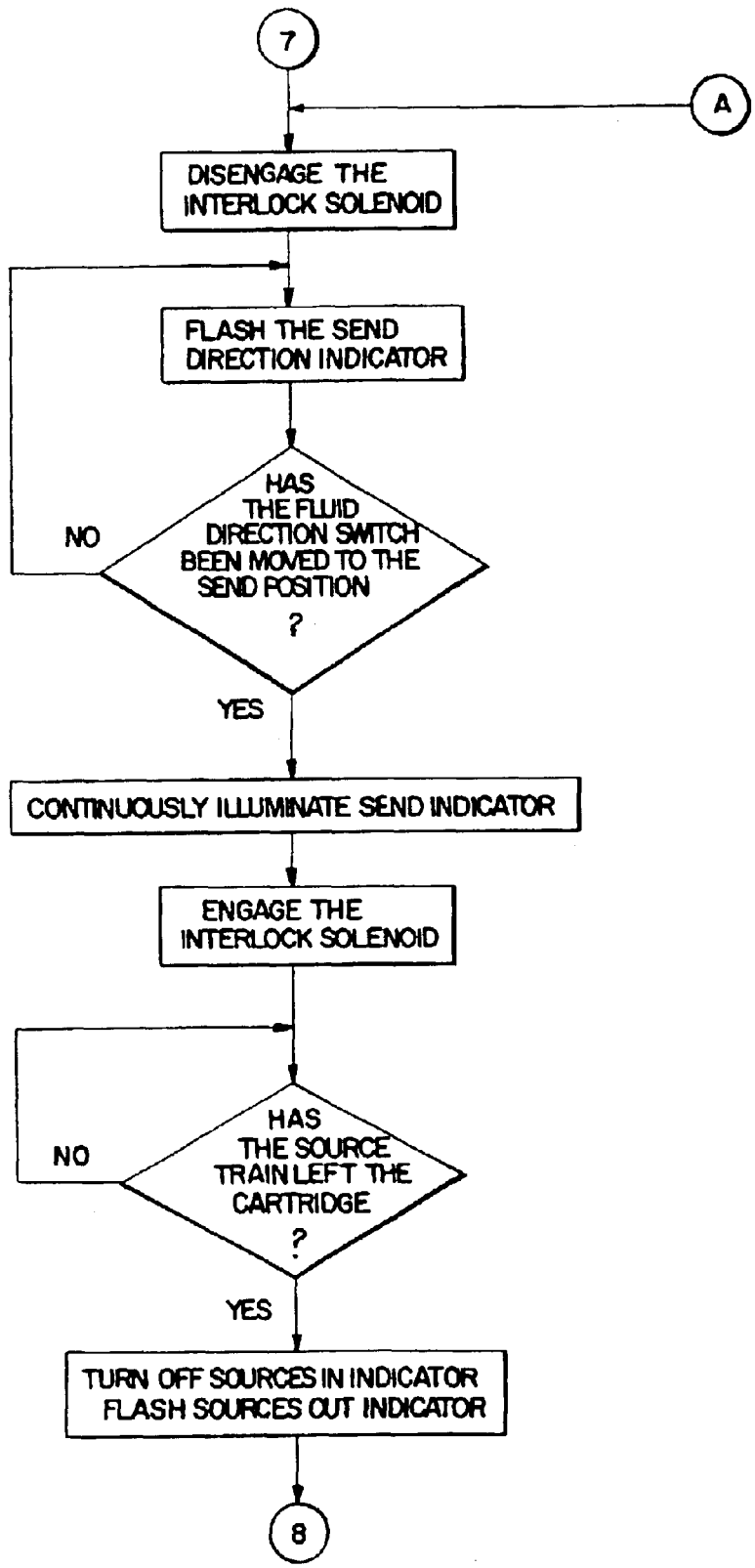
Figure 10H:
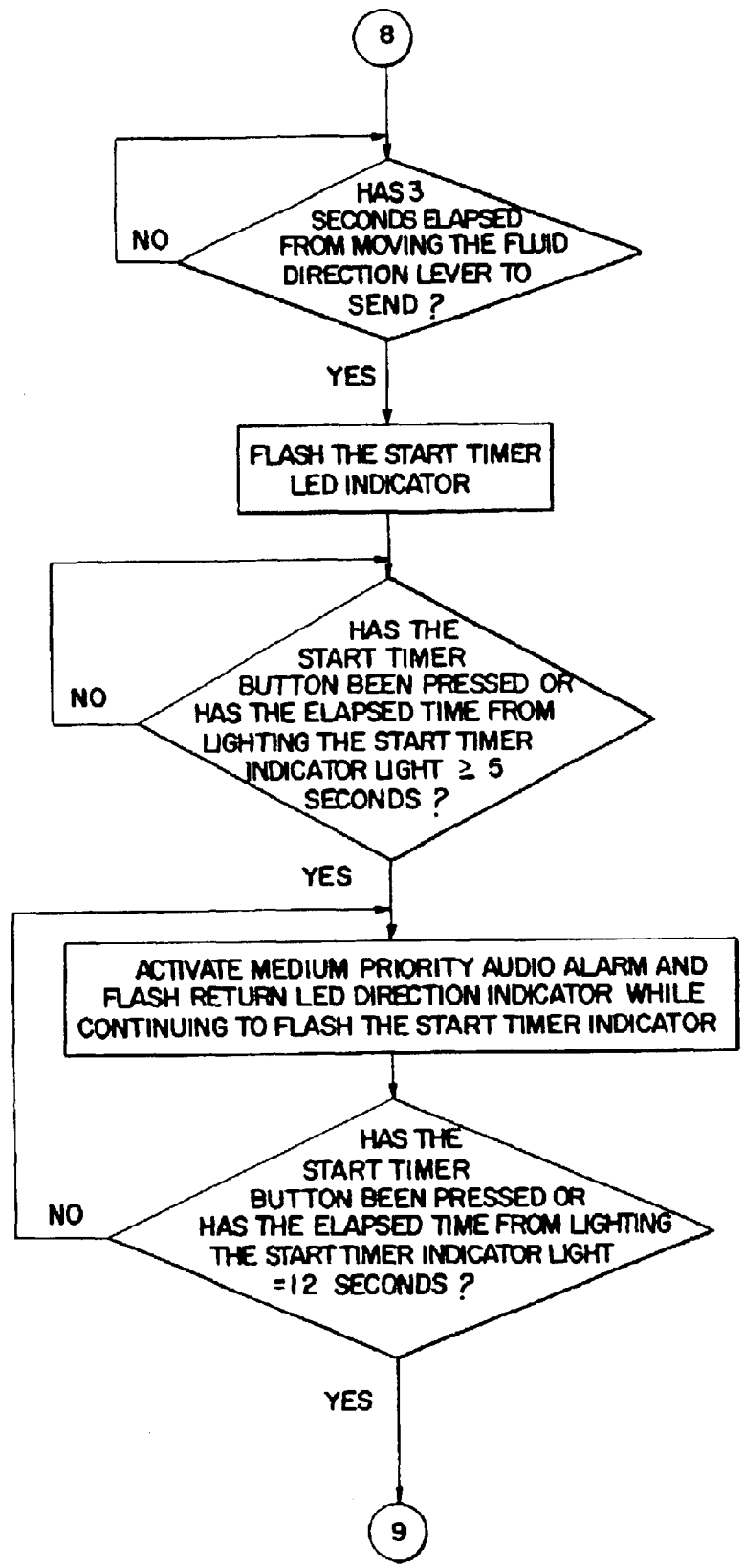
Figure 10:
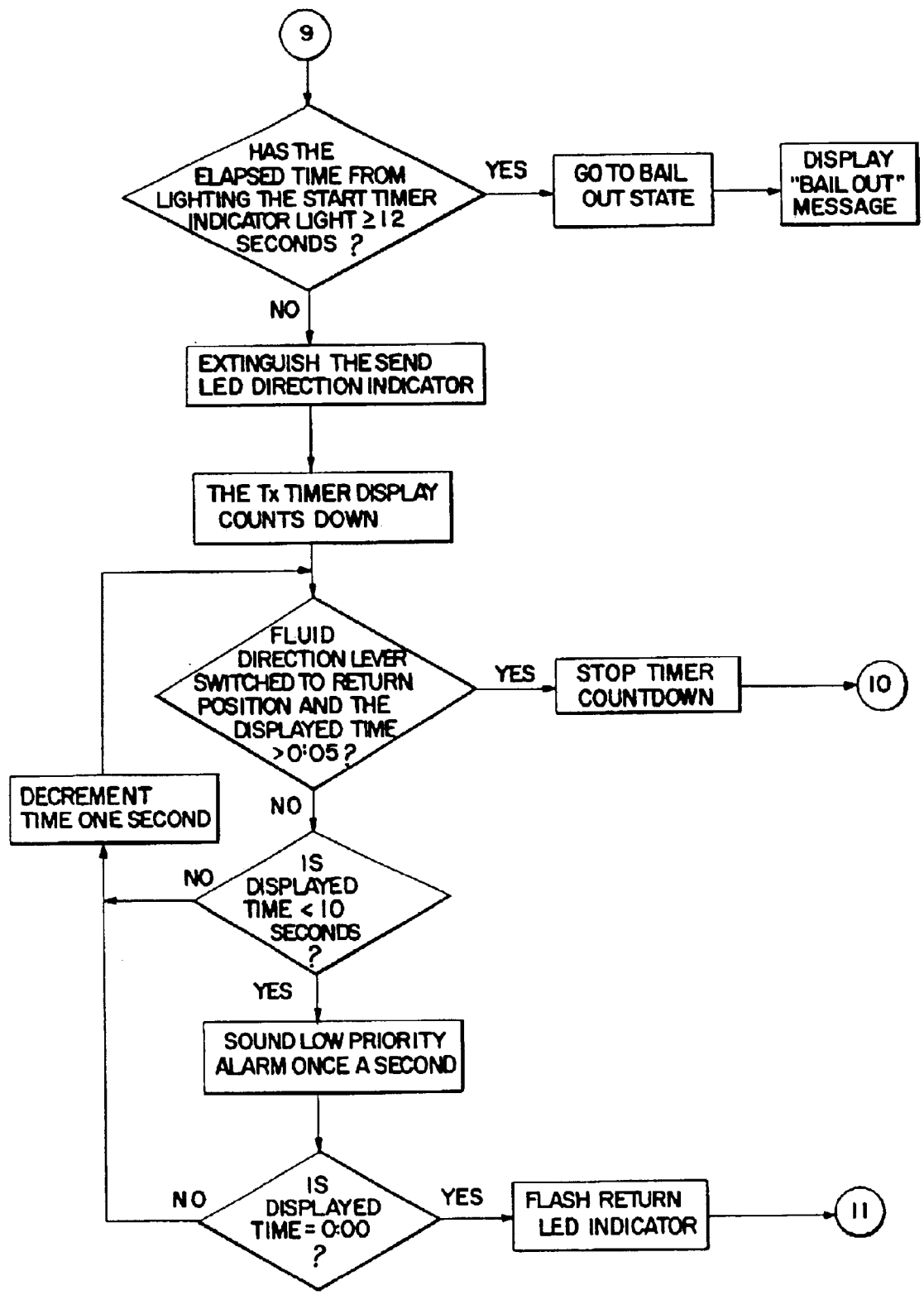
Figure 10J:
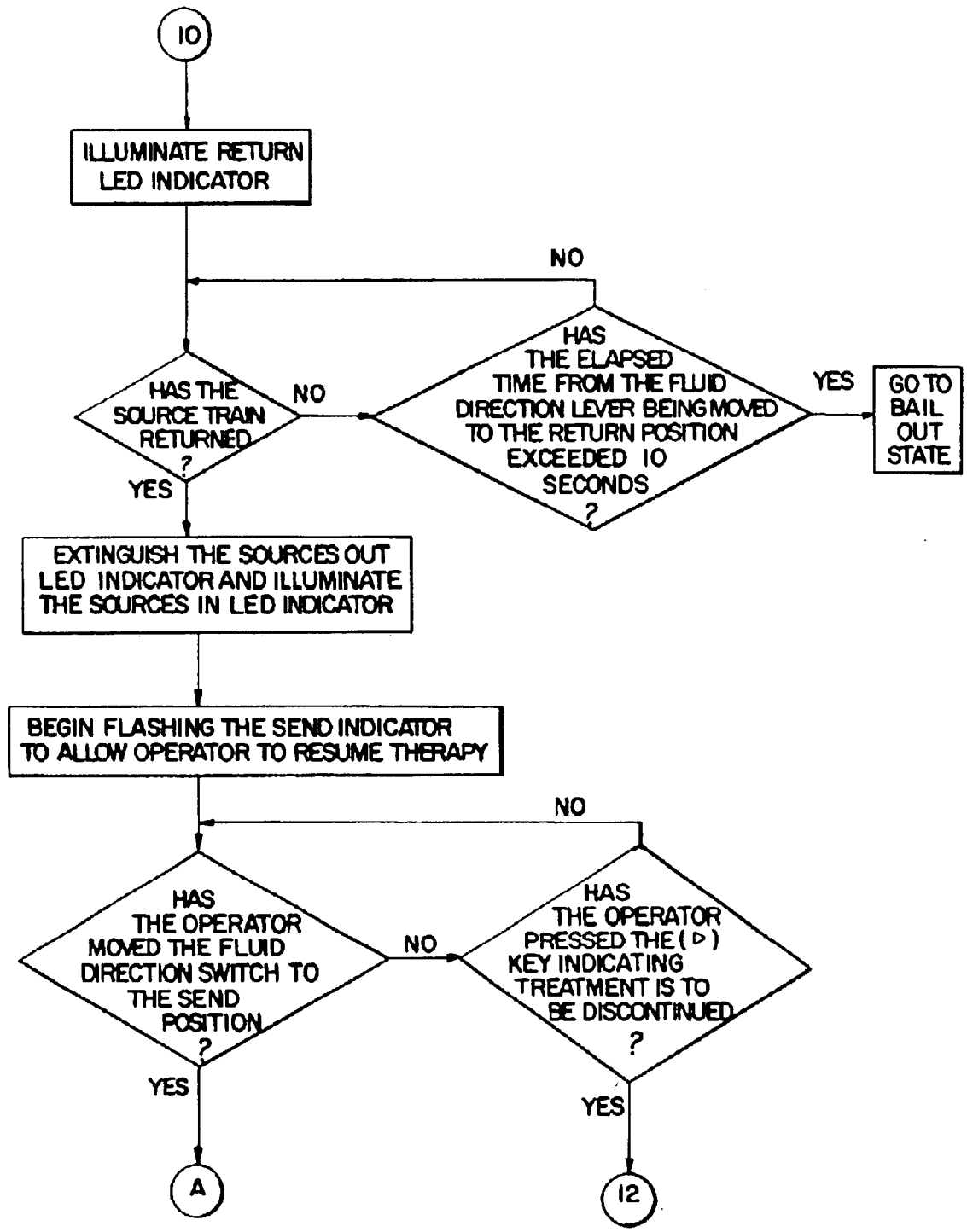
Figure 10K:
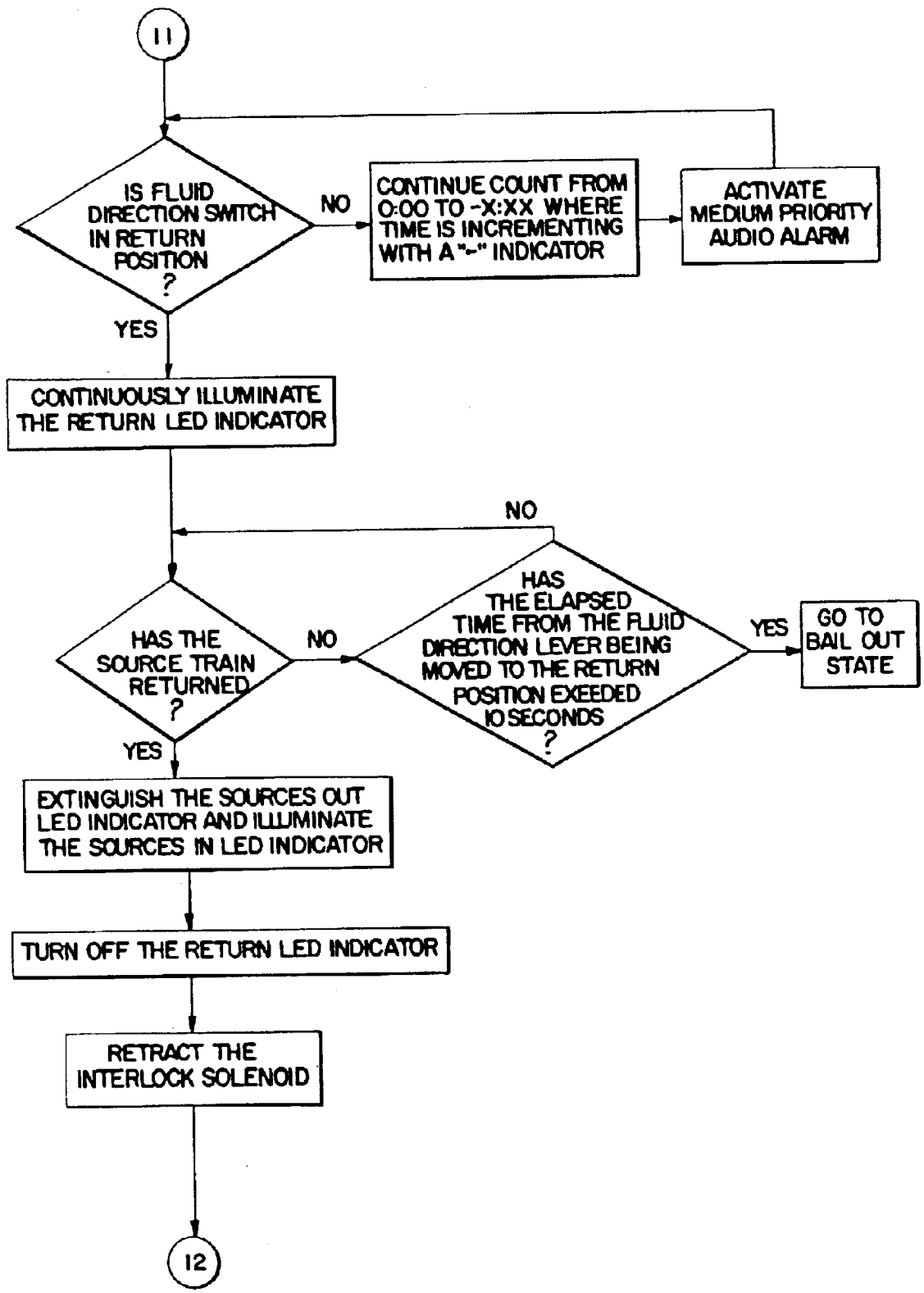
Figure 10L:
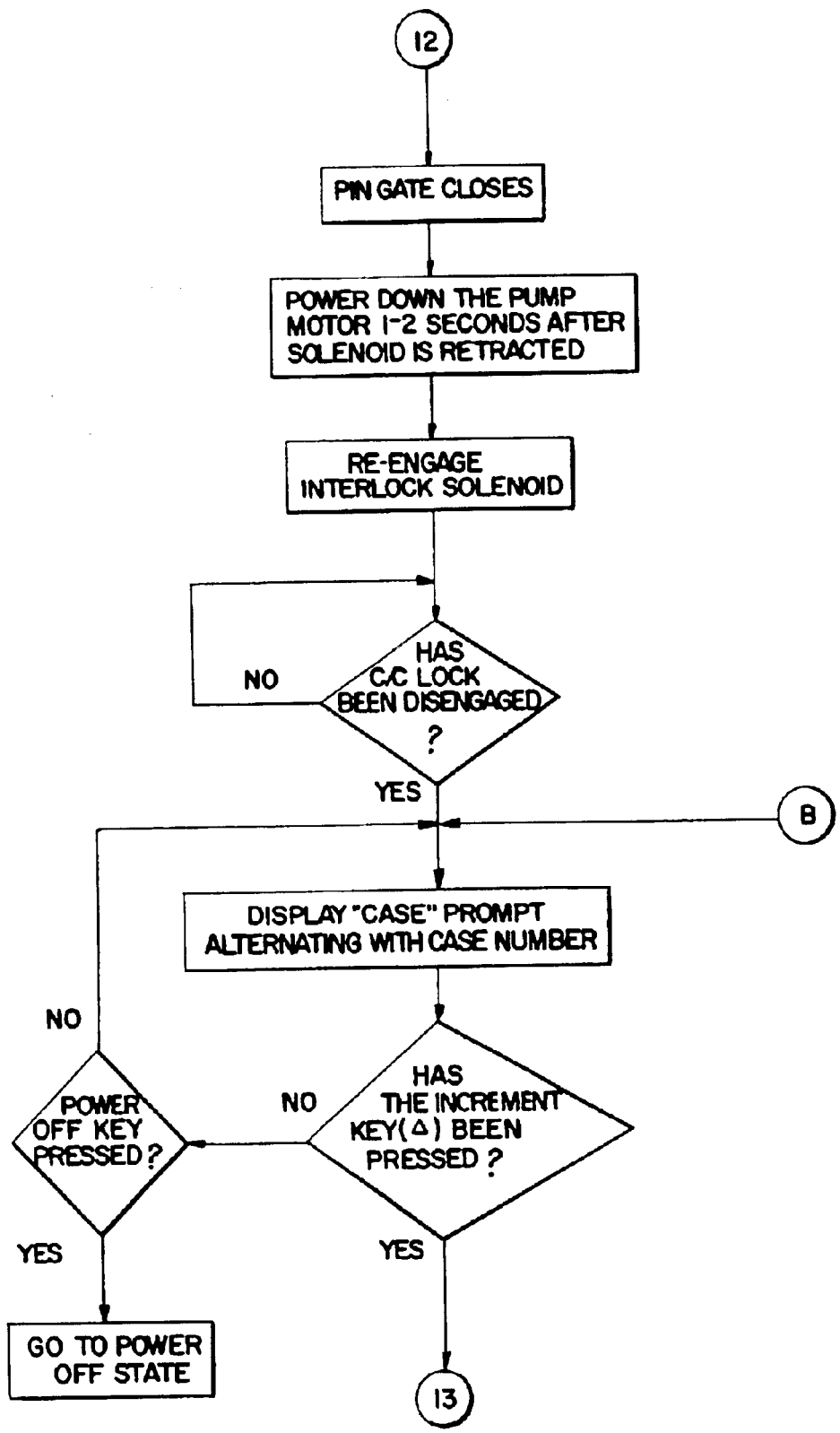
Figure 10M:
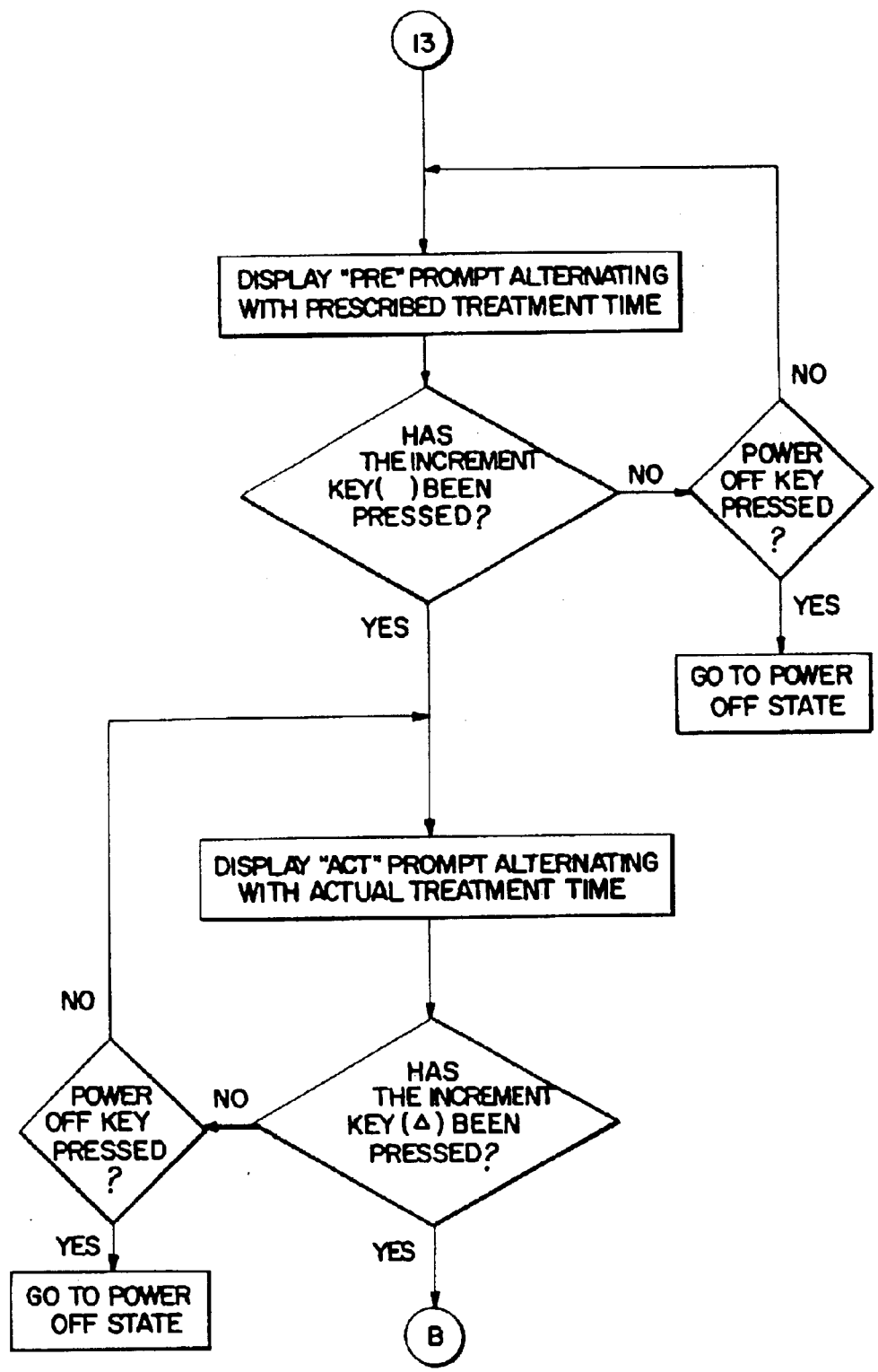
Figure 11:
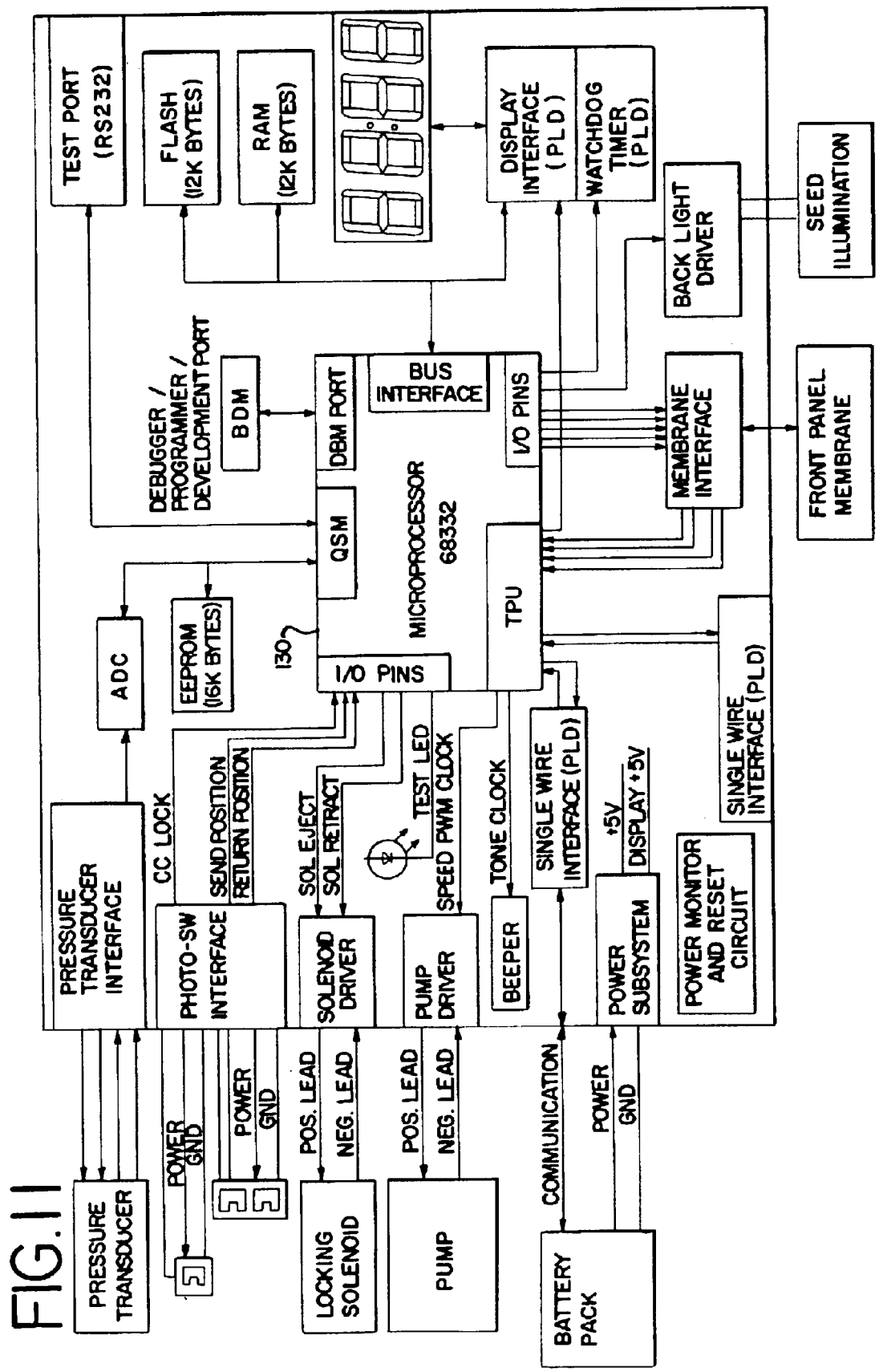
FIG. 11 is a schematic diagram of the system electronics for the transfer device of FIG. 1.
Figure 12A:
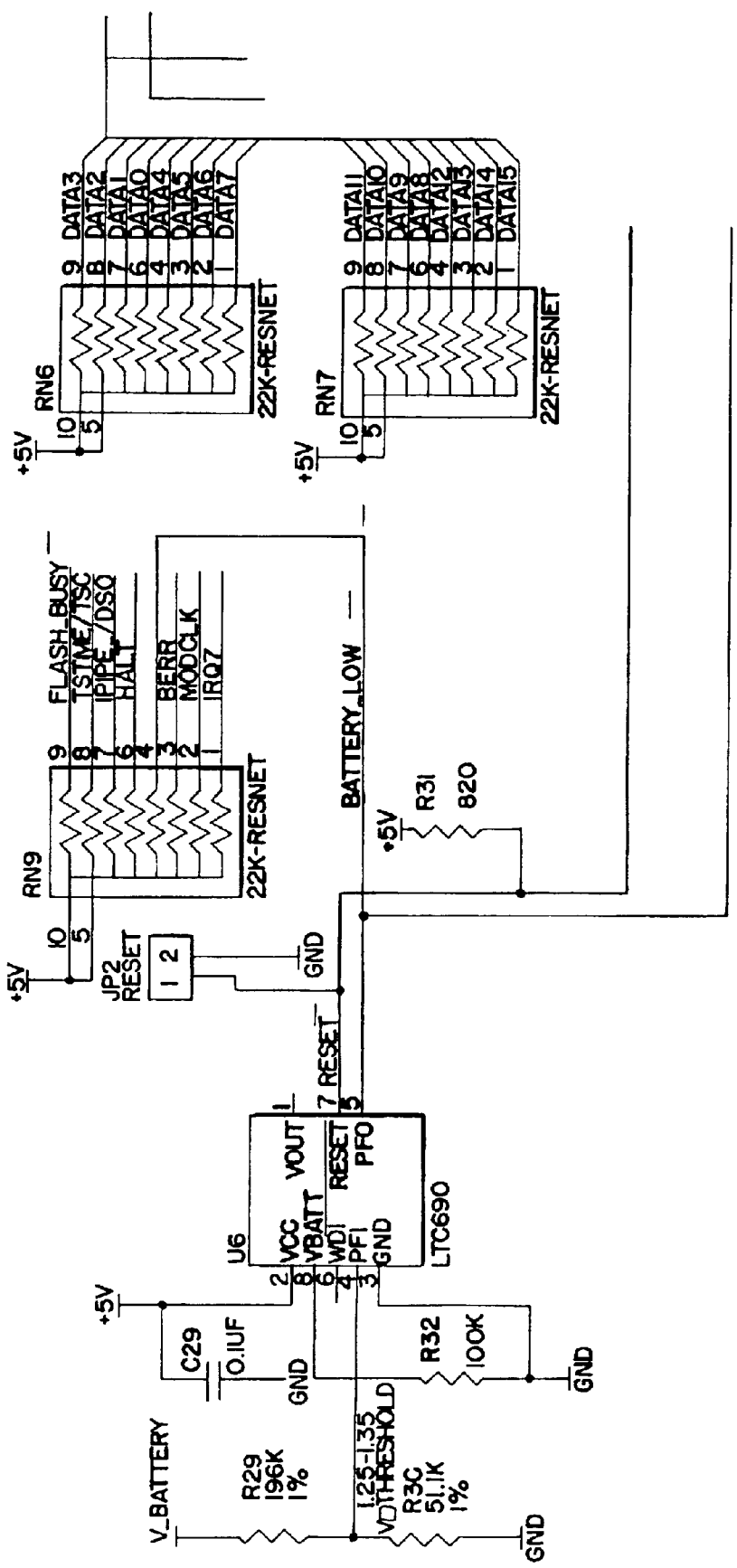
Figure 12B:
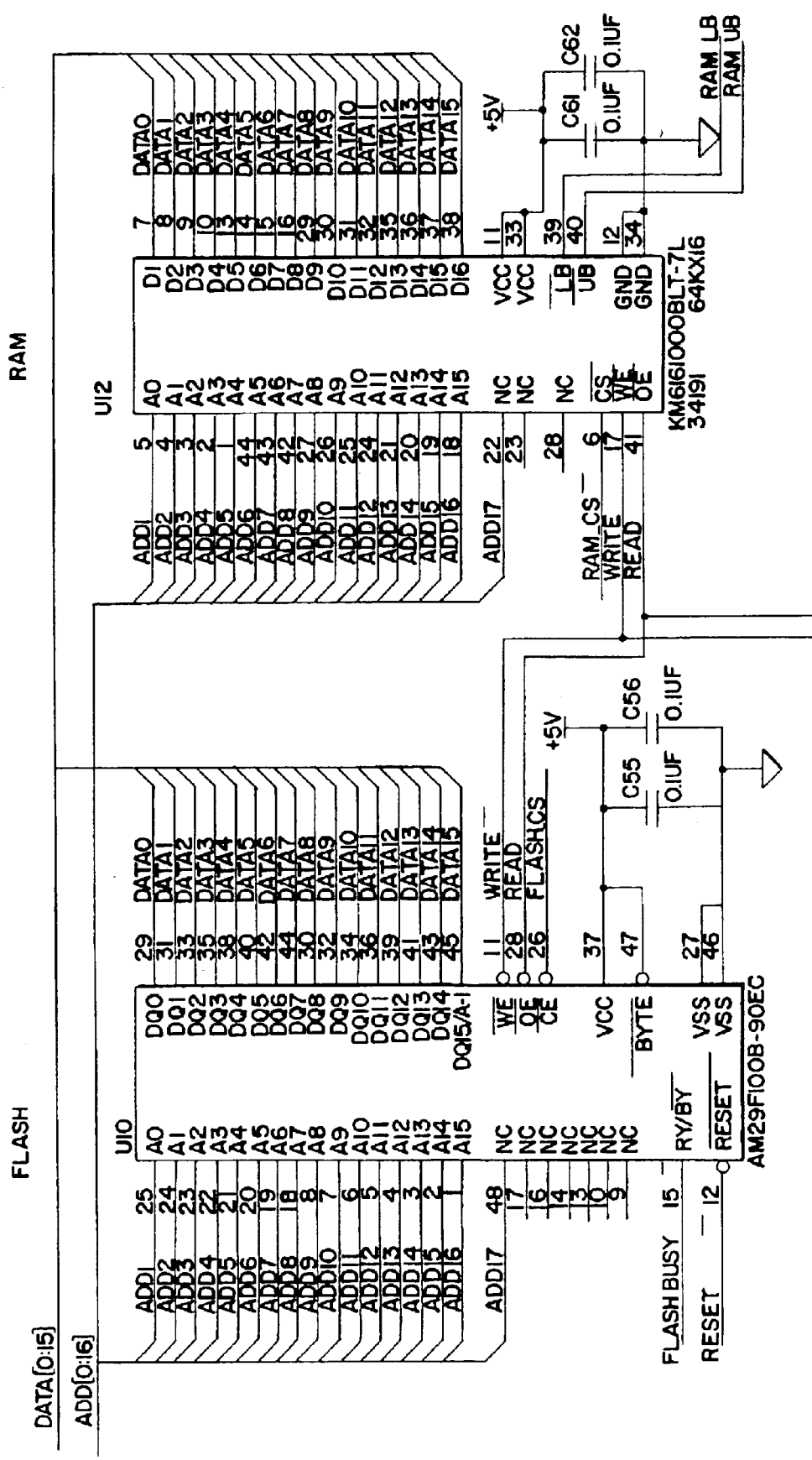
Figure 12C:
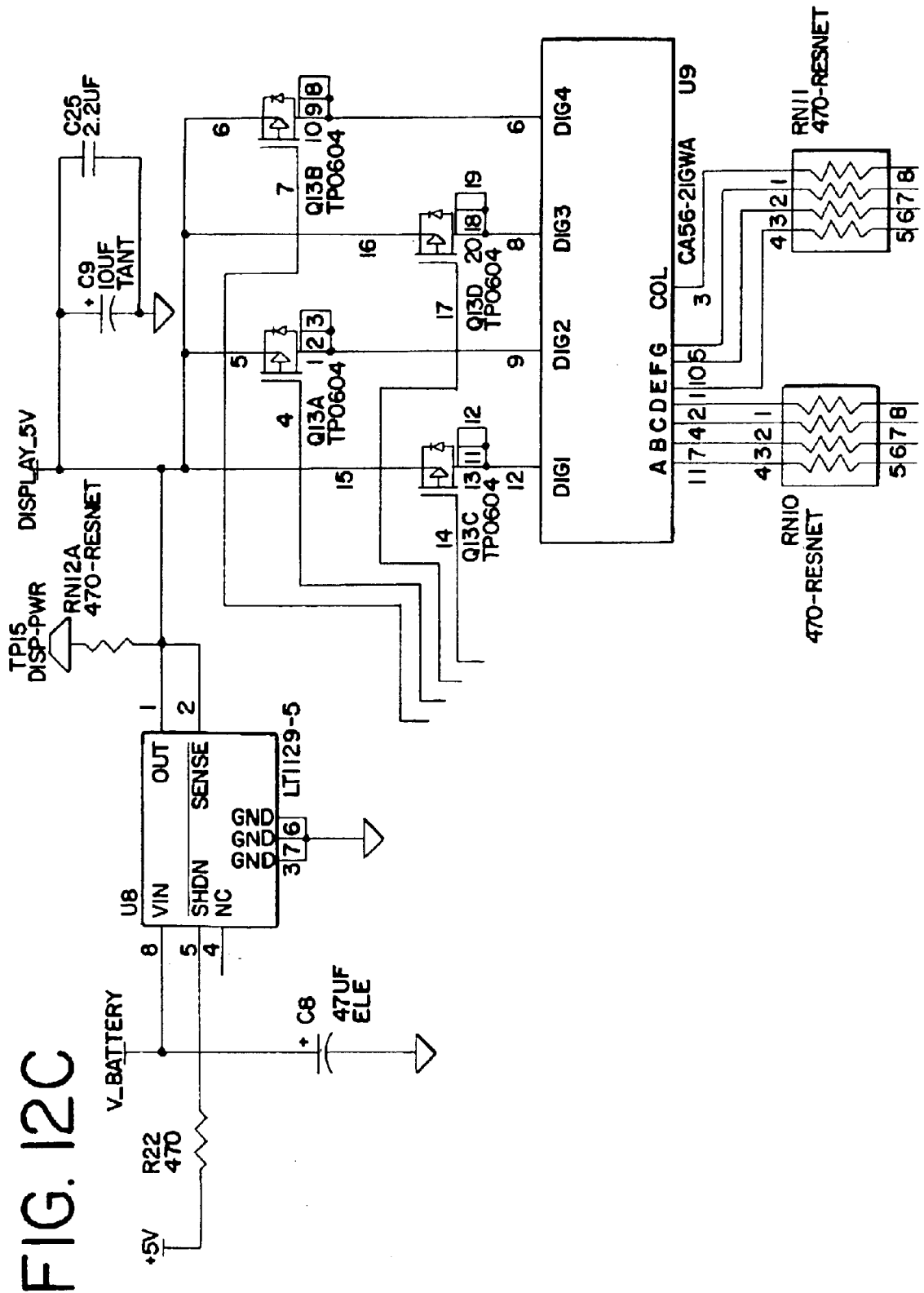
Figure 12D:
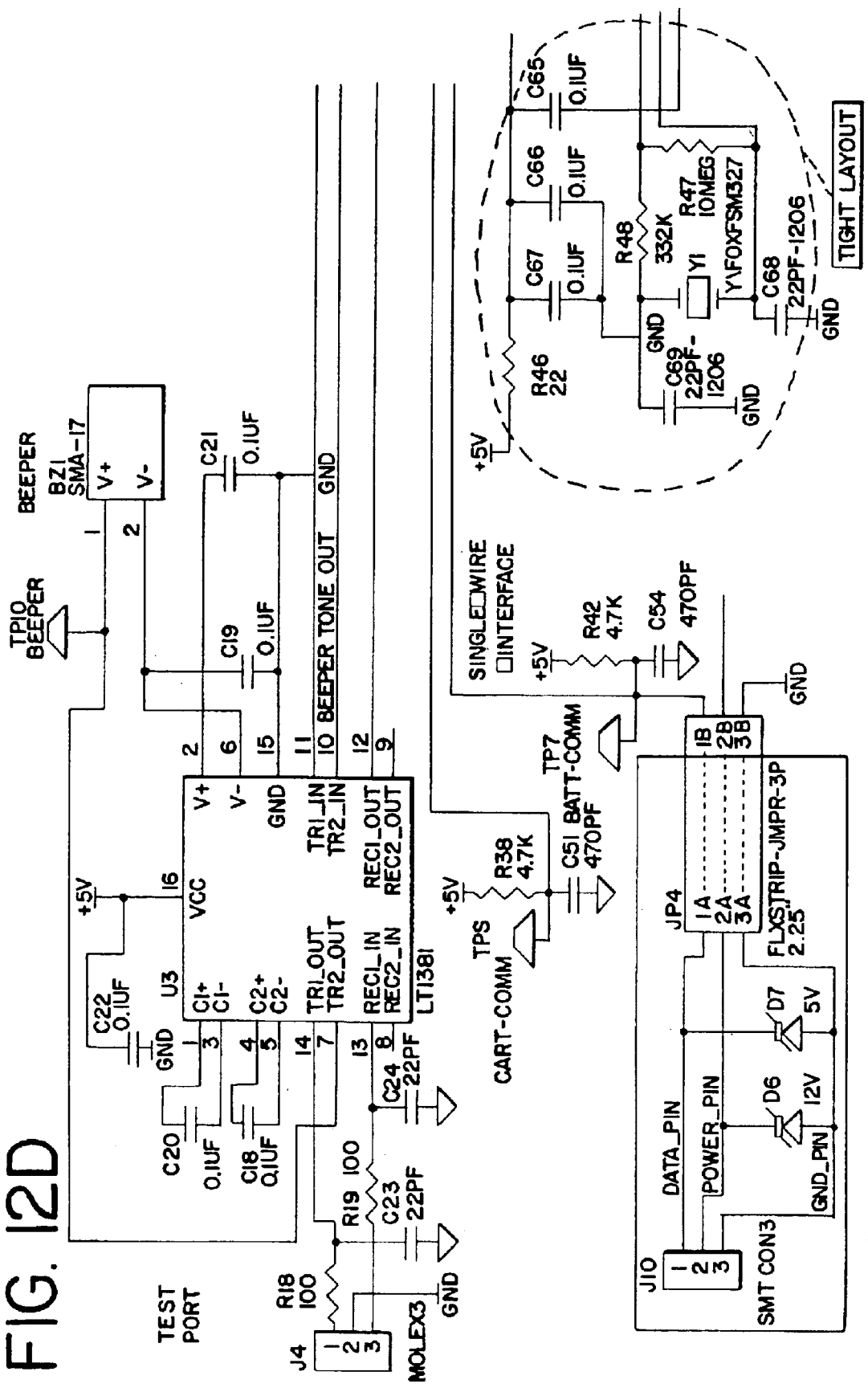
Figure 12E:
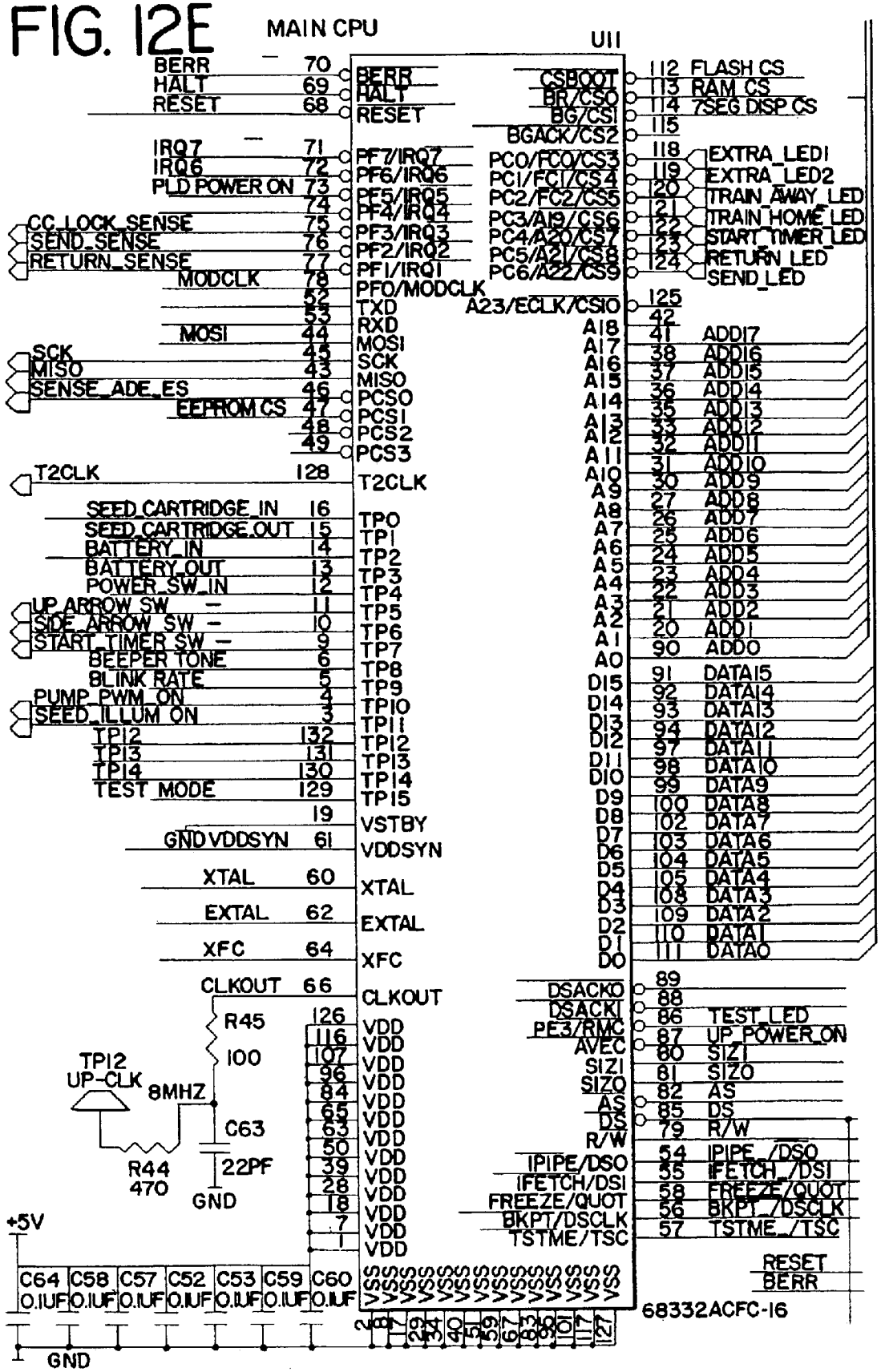
Figure 12F:
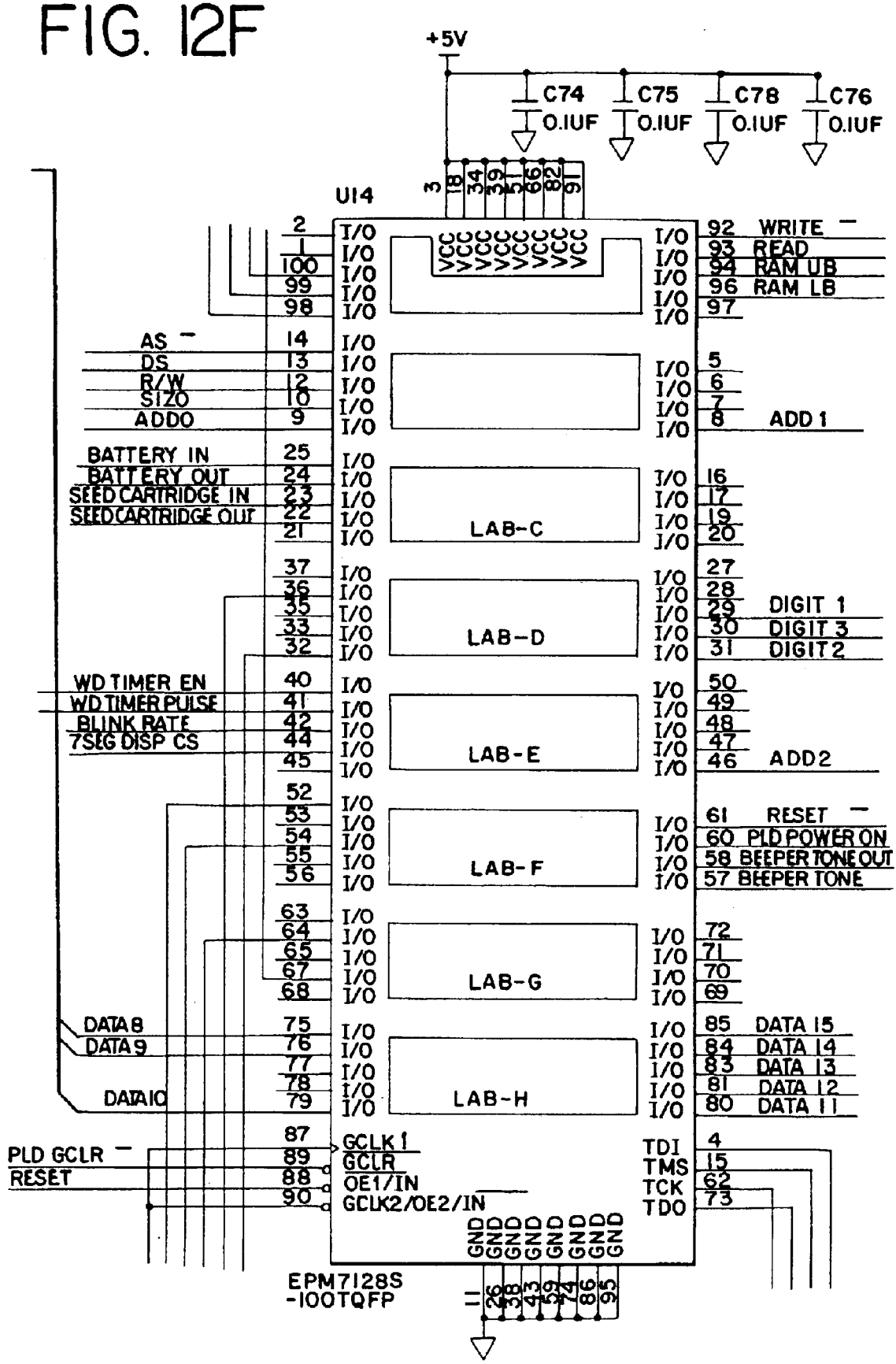
Figure 12H:
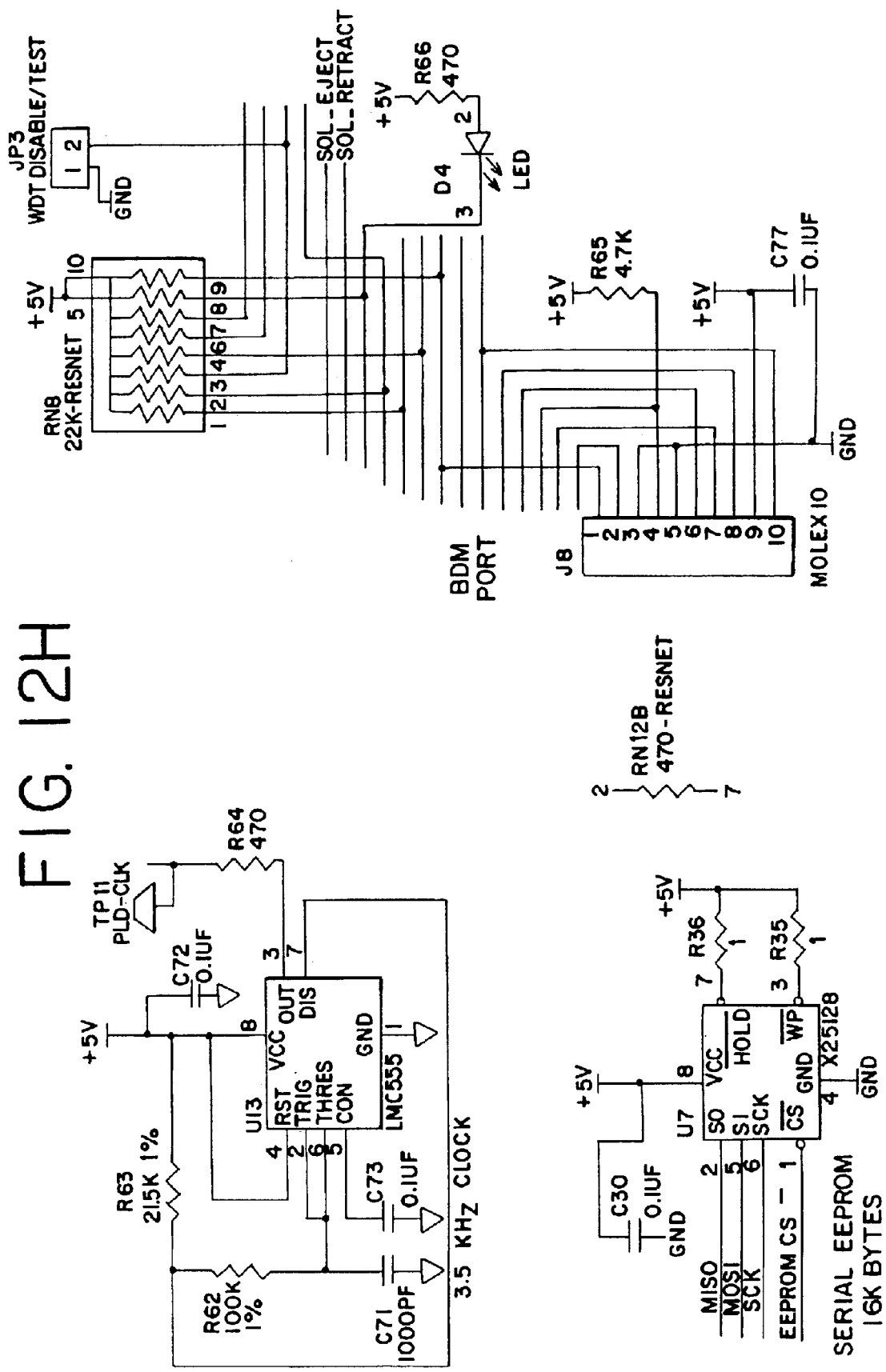
Figure 12I:
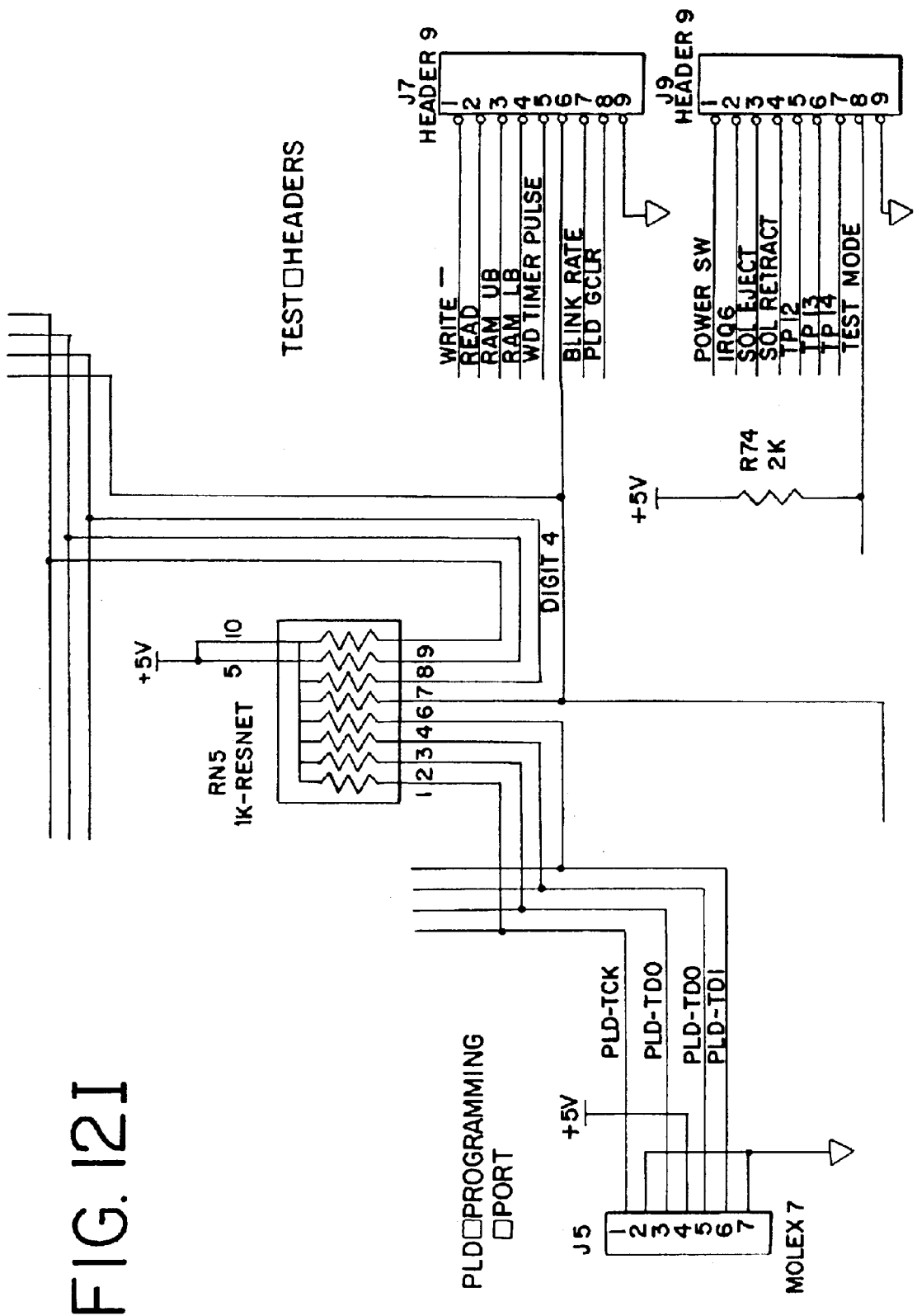
Figure 12J:
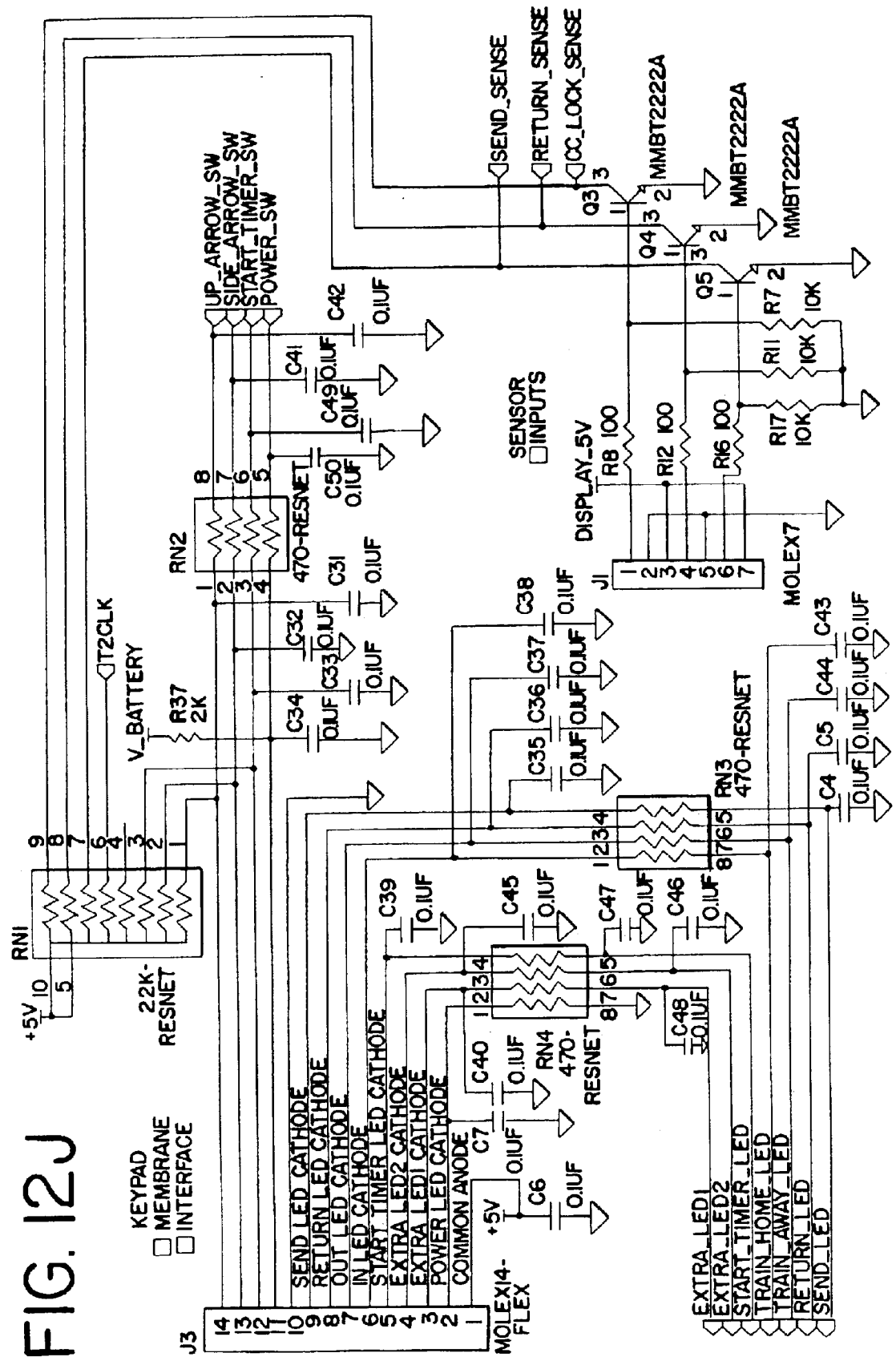
Figure 12K:
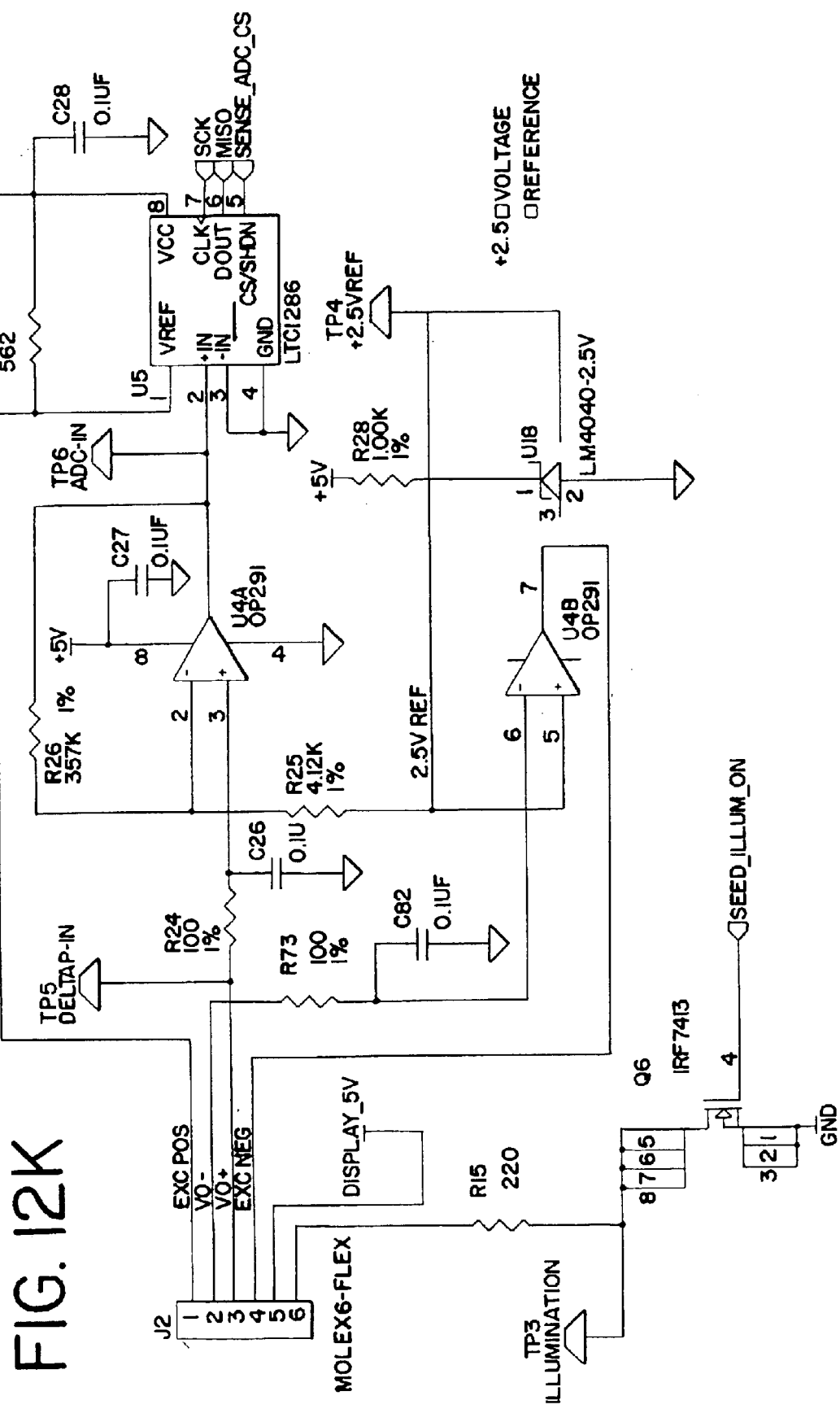
Figure 12L:
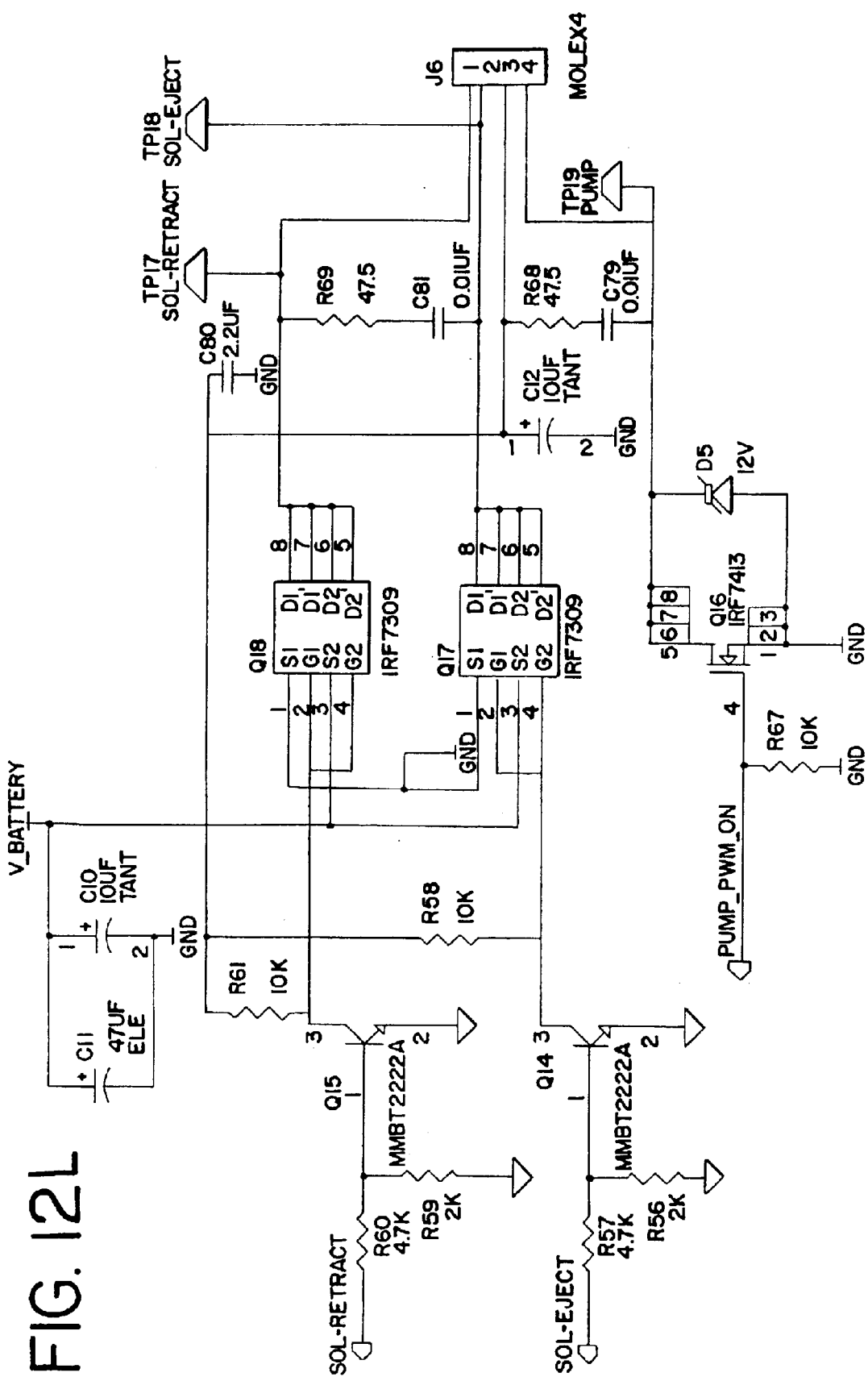

With reference to FIGS. 10A–M, there is seen a flow chart that illustrates the logic programming of the microprocessor incorporated into the transfer device for controlling its operation. The flow chart takes the operator through a series of steps, starting with FIG. 10A where the transfer device is turned on, to turning off the transfer device after completion of a procedure, in FIG. 10M, and shows the messages generated for display on the LED 26.

A schematic diagram and a circuit diagram of the electronics are shown in FIGS. 11 and 12A–L, respectively. The electronics are built onto one printed circuit board, which is sealed within a tray 128 by the membrane keypad 37. The electronic circuitry includes a microprocessor 130 and controls the pressure transducer 88, solenoid 124, pump 60, battery pack 46, sensors, beeper or audio alarm, display interface, membrane interface, and back lighting for source train illumination.

Accordingly, an intraluminal radiation treatment system has been disclosed that meets all the objects of the invention. While the system has been described in terms of a preferred embodiment, there is no intent to limit the invention to the same. Instead, the invention is defined by the following claims.

That which is claimed:

1. In a system comprising a microprocessor-controlled transfer device and a separate catheter for intraluminal treatment of a selected site in a body of a patient by at least one treating element advanced from a removable treating element cartridge received in the transfer device into a lumen of the separate catheter by means of pressurized fluid controlled by a fluid control switch moveable between send and return positions, a safety interlock for preventing both the disassembly of the system unless the treating element resides in the treating element cartridge and the actuation of the fluid control switch unless the system is assembled, the safety interlock comprising:

a first lock removeable from a first position to a second position only if both the catheter and treating element cartridge are secured to the transfer device, the first lock blocking movement of the fluid control switch to the send position when in the first position and preventing disassembly of either the catheter or the treating element cartridge from the transfer device when in the second position, the fluid control switch further locking the first lock in its second position when the fluid control switch is in the send position.

2. The safety interlock of claim 1 wherein the first lock comprises:

a spring having two arms, each arm being engaged by one of the catheter or the treating element cartridge when attached to the transfer device; and a slidable switch including a yoke that is moveable from a first position to a second position to capture the arms of the spring and lock both the catheter and treating element cartridge to the transfer device only if each arm of the spring is engaged by one of the catheter and treating element cartridge, each arm of the spring independently capable of blocking movement of the yoke from the first position to the second position if not engaged by one of the catheter or treating element cartridge.

3. The safety interlock of claim 2 wherein the slidable switch includes a shoulder and the fluid control switch includes an arm that engages the shoulder when the yoke is in the second position and the fluid control switch is in the send position.

4. A safety interlock of claim 1 further comprising:

a gate mechanism moveable between open and closed positions by the fluid control switch to respectively permit or prevent the treating element from moving out of the treating element cartridge when subjected to a pressurized fluid; and a solenoid to lock the gate mechanism in the open position, the solenoid disengaging the gate mechanism to permit it to close only when the treating element resides in the treating element cartridge.

5. The safety interlock of claim 1 further comprising:

a photo interrupter that is triggered when the first lock is moved to the second position to lock the treating element cartridge and the catheter to the transfer device, the triggered photo interrupter generating a signal that is transmitted to the microprocessor to permit the treatment to continue.

6. The safety interlock of claim 4 further comprising a series of photo interrupters associated with the fluid control switch to detect the position of the fluid control switch and generate a signal sent to the microprocessor to permit the treatment to continue in accordance with the position of the fluid control switch.

* * * * *